(12) United States Patent
Ellis-Davies

(10) Patent No.: US 8,642,785 B2
(45) Date of Patent: Feb. 4, 2014

(54) PHOTOLABILE DINITROINDOLINYL BASED COMPOUNDS

(75) Inventor: Graham Ellis-Davies, Philadelphia, PA (US)

(73) Assignee: Philadelphia Health & Education Corporation, Philadelphia, PA (US)

( * ) Notice: Subject to any disclaimer, the term of this patent is extended or adjusted under 35 U.S.C. 154(b) by 454 days.

(21) Appl. No.: 12/520,924

(22) PCT Filed: Jan. 29, 2008

(86) PCT No.: PCT/US2008/052331
§ 371 (c)(1),
(2), (4) Date: Jun. 23, 2009

(87) PCT Pub. No.: WO2008/094922
PCT Pub. Date: Aug. 7, 2008

(65) Prior Publication Data
US 2010/0096252 A1    Apr. 22, 2010

Related U.S. Application Data

(60) Provisional application No. 60/887,530, filed on Jan. 31, 2007.

(51) Int. Cl.
*C07D 209/04*    (2006.01)

(52) U.S. Cl.
USPC ........................................ 548/491

(58) Field of Classification Search
USPC ........................................ 548/491
See application file for complete search history.

(56) References Cited

FOREIGN PATENT DOCUMENTS

WO    2004085394 A1    10/2004

OTHER PUBLICATIONS

Papageorgiou, et al., Document No. 145:336277, entered in STN on Oct. 27, 2005, retrieved from CAPLUS.*
Ellis-Davies, et al. Document No. 143:286657, Jul. 19, 2005, retrieved from CAPLUS.*
Helgen, et al. Document No. 136:309473, Dec. 27, 2001, retrieved from CAPLUS.*
Adams, et al. Document No. 111:232230, Dec. 23, 1989.*
Papageorgiou, et al. Document No. 145:336277, Oct. 27, 2005, retrieved from CAPLUS.*
Papageorgiou et al., "Synthetic and photochemical studies of substituted 1-acyl-7-nitroindolines", Photochem. Photobiol. Sci., vol. 4, pp. 887-896 (2005).
International Search Report for PCT/US2008/052331, Jul. 2, 2008.

* cited by examiner

*Primary Examiner* — Shawquia Young
(74) *Attorney, Agent, or Firm* — Mendelsohn, Drucker & Dunleavy, P.C.

(57) ABSTRACT

The present invention relates to photolabile or photoreleasable compounds including a caging moiety linked to an effector moiety, wherein the compounds are capable of releasing the effector moiety on irradiation, typically by flash irradiation with UV light. These compounds are particularly suitable for focal 2-photon uncaging The photoreleasable compounds can be used to deliver effector moieties such as carboxylic acids, preferably, neuroactive amino acids to sites where their activity is required. In preferred embodiments of the invention, the caging moiety is based on 4-carboxymethoxy-5,7-dinitroinlinyl and derivatives thereof.

5 Claims, 8 Drawing Sheets

CNI-GABA

MNI-Glu <span></span> CDNI-Glu

MNI-Glu <span></span> CDNI-Glu

PHOTOLABILE DINITROINDOLINYL BASED COMPOUNDS

STATEMENT REGARDING FEDERALLY SPONSORED RESEARCH OR DEVELOPMENT

This research was supported in part by U.S. Government funds (National Institute of Health, Grant No. 1 R24 GM65473-02) and the U.S. Government may therefore have certain rights in the invention.

BACKGROUND OF THE INVENTION

1. Field of Invention

This invention relates to photolabile compounds and processes for making and using these compounds.

2. Description of Related Art

Light is an essential tool for studying cells. High photonic fluxes are often required to acquire a distinct signal in fluorescence microcopy, but such high power can also disrupt cells (by heating, singlet oxygen production, etc.), and bleach endo/exogenous chromophores. Photolabile "caged" compounds are inert precursors of bioactive molecules that can be loaded into cells and later released in their active form. Photochemical uncaging of biological signaling molecules typically uses brief bursts of light (near-UV wavelengths for regular, one-photon uncaging, or near-IR light for 2-photon photolysis). This mechanism is highly advantageous in studying the kinetics of important signaling events such as, for example, activation of receptors and ion channels and release of neurotransmitters.

U.S. Pat. No. 6,765,014 describes 7-nitroindoline compounds. In section 24, compound 35 is mentioned

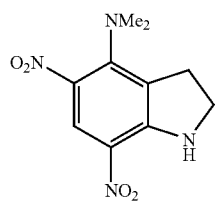 [SMILES: CN(C)c1c([N+](=O)[O-])cc([N+](=O)[O-])c2c1CCN2]

among potential candidates for coupling to an effector molecule. However, it is known that the presence of an amino substituents on the nitroaromatic chromophore creates a very low-lying triplet state of the chromophore, and quenches reactivity (Schuddeboom, W. et al., Dipolar Triplet States of p-Nitroaniline and N-Alkyl Derivatives with One-, Two-, and Three-Fold Symmetry *J. Phys. Chem.* (1996) 100, 12369). Furthermore, it is known that sterically hindered aromatic amines cannot be acylated, even under the best activating condition (Katritzky et al., N-Acylbenzotriazoles: Neutral Acylating Reagents for the Preparation of Primary, Secondary, and Tertiary Amides Org. Chem. 2000; 65, 8210-8213). This is especially true of such amines that are strongly deactivated by one or two electron withdrawing groups that are in the ortho and/or para positions of the aromatic ring. Therefore, dinitroanilines such as compound 35 require radical changes to their structures to make them useful photochemically and synthetically. Therefore, the compound 35 cannot be coupled to an effector molecule without a loss of a nitro group in the $5^{th}$ position.

WO04085394A1 to Corrie et al. describes 7-nitroindoline compounds which include a triplet sensitizing group such as substituted or unsubstituted benzophenone group and can be used to cage neurotransmitter effector species.

U.S. Pat. Nos. 5,430,175 and 5,587,509 to Hess et al. describe caged carboxyl compounds and methods of releasing carboxyl compounds in which a 2-alkoxy-5-nitrophenyl photosensitive group blocks a carboxyl function. Preferred compounds are caged neuroactive amino acids (e.g., glutamate and gamma-aminobutyric acid (GABA)) with carboxynitrobenzyl chromophores (CNB) photolyzable by laser pulses at wavelengths above about 350 nm within about 3 microseconds and provide a product quantum yield of greater than about 0.2.

The balance between excitatory and inhibitory signaling in the CNS is fundamental to the incredible complexity required for neuronal computation. Chemical synapses are activated by the release of glutamate (Glu), the major excitatory transmitter. This activation is sculpted in many significant ways by the release of γ-aminobutyric acid (GABA), the major inhibitory transmitter. GABA may be released either onto the postsynaptic cell or directly onto a glutamatergic pre-synaptic cell in order to modulate the effects of glutamate release. In the immature brain, GABA is the main excitatory transmitter. GABA releasing synapses are formed before glutamatergic contacts, in many different animals and types of synapses. At some point during development there is an activity-dependent switching from excitation to inhibition by GABAergic synapses.

What is the reason for continued focus on cage development? A brief survey of this history reveals why there is still compelling need for an improved caged glutamate. The first good caged glutamate was CNB-Glu (Weiboldt, et al., 1994). UV-laser excitation released glutamate quickly and with usable efficiency from this caged compound. However, the unadorned ortho-nitrobenzyl chromophore has a very low 2-photon cross section (value of less than 0.001 GM [1 GM=$10^{-50}$ cm$^4$s/photon]), and CNB-Glu is some what hydrolytically unstable being a benzyl ester. For this reason, Bhc- and DMCNB-Glu were synthesized (Furuta et al., 1999; Ellis-Davies, 1999). The former has a large 2-photon cross section and is totally stable at pH 7.4, however the rate of glutamate photorelease is far too slowly for focal 2-photon uncaging (instead irradiation produces a "mist" of glutamate). The latter releases glutamate quickly and efficiently enough for single spine stimulation but is too unstable in solution before illumination to be impractical for day-to-day use. MNI-Glu was synthesized to solve this latter problem as the benzamido bond is quite stable (solutions stored at 4° C. for 2 d show no detectable hydrolysis, and showed 1% hydrolysis after 13 d, during this time CDNI-Glu had hydrolyzed 7%), and the chromophore preserves the photochemical efficiency of the DMCNB cage. However, when used for 2-photon photolysis MNI-Glu is applied at high concentrations (5-12 mM) that must be irradiated with powers at the very limit of tolerance for brain tissue (Matsuzaki, et al., 2004). For this reason, an even better caged glutamate is desired. An NI-Glu derivative was made containing a cross-linked benzophenone chromophore ("antenna-NI-Glu", Papageorgiou, et al., 2004). When UV light (300-308 nm) was used to excite the benzophenone antenna, triplet energy transfer to the MNI cage released glutamate with high efficiency, which dropped considerably (ca. 2.5-fold) at 354 nm. Most microscopes do not have a 300-nm laser (standard Ar—Kr lasers emit at 354-363 nm) or quartz optics required for transmission in this region. In contrast, the inventor was able to uncage CDNI-Glu at 354 nm with very high efficiency (similar to the antenna-NI-Glu at 300 nm).

The first caged GABA was made in 1994 (Gee, et al., 1994), by the same group that synthesized CNB-Glu. CNB-GABA has been used by a few groups to study the activation of GABA receptors (Jayaraman, et al., 1999) and to attempt to map the distribution of these receptors in brain on CA1 neurons (Pettit & Augustine, 2000; Eder, et al., 2001). However, even though laser flash photolysis of CNB-GABA suggested that the neurotransmitter is released with a half-time of about 30 microseconds (Gee, et al., 1994), when used to activate currents in outside-out membrane patches with a 10-90% rise time of about 8 ms (Jayaraman, et al., 1999). This latter value is in stark contrast to the values recorded from stellite cells in cerebellar brain slices of 0.4 ms (Nusser, et al., 1997). Rapid flow of saturating [GABA] onto excised outside-out patch using piezo electric devices have given times in the 0.4-0.9 ms (Mozrzymas, et al., 2002; Jones, et al., 1998). Activation of GABA receptors in situ in neurons in brain slices by UV uncaging of CNB-GABA has given rise-times (Pettit & Augustine 2000) that were even slower than excised patches (Jayaraman, et al., 1999). The size of the uncaging spot may contribute to this poor temporal resolution, or the lack of visually identified receptor clusters (as with AMPA receptors on spine heads). The former problem gives a large volume for release that could activate multiple synapses at different distances and times, whilst the latter problem would require uncaged GABA to diffuse after release to the receptor cluster before generating a current; either way poor temporal resolution could be produced. The new caged GABAs as made in accordance with this disclosure and tested in brain slices give the best results so far when judged in terms of how close uncaging can come to mimicking IPSC (compare FIGS. 5 A & B).

Methoxynitroindoline-caged L-glutamate (Papageorgiou & Corrie; Matsuzaki, et al., 2001) and D-aspartate (Huang, et al., 2005) has proved exceptionally useful for neuroscientists and have supplanted the previous generation of CNB-caged compounds.

However, despite the current developments, new much more photoreactive caged transmitters are desired.

All references cited herein are incorporated herein by reference in their entireties.

BRIEF SUMMARY OF THE INVENTION

In a first aspect, the invention comprises a photolabile compound comprising a chromophore having a structure depicted by the formula:

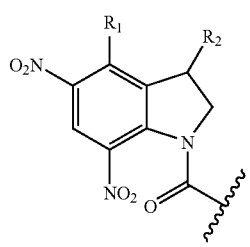

(I)

wherein $R_1$ is H, $O(CH_2)_nCO_2H$, $O(CH_2)_nOPO(OH)_2$, $O(CH_2)_nOSO_2(OH)$, $O(CH_2)_nC(O)NR_3$, $(CH_2)_nCO_2H$, $(CH_2)_nOPO(OH)_2$, $(CH_2)_nOSO_2(OH)$, $(CH_2)_nC(O)NR_3$, $C_{1-10}$ alkyl or substituted alkyl, $O(CH_2)_n$—Y, $N(COZ)(CH_2)_mY$, or $N[(CH_2)_mQ][(CH_2)_nY]$, provided that $R_1$ is not OMe, $R_2$ is H, $(CH_2)_nCO_2H$, $(CH_2)_nOPO(OH)_2$, $(CH_2)_nOSO_2(OH)$, $(CH_2)_nC(O)NR_3$ or $(CH)_nN(R_3)_2$, $R_3$ is H, Me or Et, n and m are independently from 1 to 10, preferably n is from 1 to 5, Q and Y are independently selected from H, $CO_2H$ or salts thereof, or $OPO_3^{2-}$, and Z is H, $C_{1-10}$ alkyl or substituted alkyl.

In certain embodiments, the photolabile compound further comprises an effector (X) to form a caged compound depicted by the structural formula:

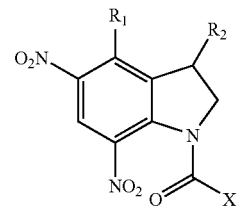

(II)

wherein X is a carboxylic acid, and $R_1$ is $O(CH_2)_nCO_2H$, $O(CH_2)_nOPO(OH)_2$, $O(CH_2)_nOSO_2(OH)$, $O(CH_2)_nC(O)NR_3$, $(CH_2)_nCO_2H$, $(CH_2)_nOPO(OH)_2$, $(CH_2)_nOSO_2(OH)$, $(CH_2)_nC(O)NR_3$, $C_{1-10}$ alkyl or substituted alkyl, $O(CH_2)_n$-M, $N(COZ)(CH_2)_mY$, or $N[(CH_2)_mQ][(CH_2)_nY]$, $R_2$ is H, $(CH_2)_nCO_2H$, $(CH_2)_nOPO(OH)_2$, $(CH_2)_nOSO_2(OH)$, $(CH_2)_nC(O)NR_3$ or $(CH)_nN(R_3)_2$, $R_3$ is H, Me or Et, n and m are independently from 1 to 10, Q and Y are independently selected from H, $CO_2H$ or salts thereof, or $OPO_3^{2-}$, M is selected from $CO_2H$ or salts thereof, or $OPO_3^{2-}$, and Z is H, $C_{1-10}$ alkyl or substituted alkyl.

In certain embodiments, the carboxylic acid is a neuroactive amino acid.

In certain embodiments, the neuroactive amino acid is at least one of L-glutamate, gamma-aminobutyric acid, D-aspartate, or glycine.

In certain embodiments, the caged compound is depicted by at least one of the following formulas:

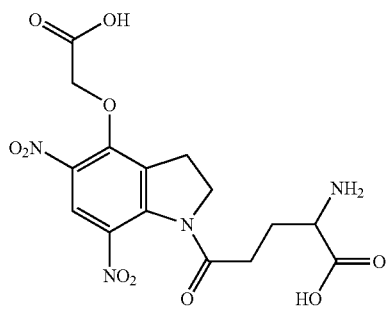

(III)

-continued

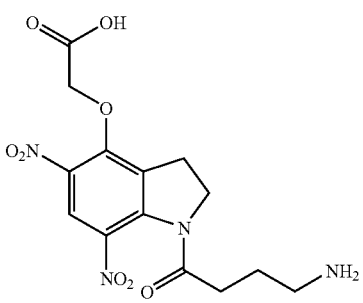
(IV)

In a second aspect, the invention comprises a method of photochemical release of an effector molecule from a caged compound, the method comprising:
(a) preparing a caged compound comprising a chromophore of claim 1 and an effector molecule X as depicted by the formula (II)

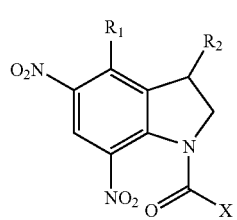
(II)

wherein X is a carboxylic acid; and (b) photolyzing the caged compound with light to release the effector molecule.

In a third aspect, the invention comprises a method of making a caged compound (1-[4-aminobutanoyl]-5,7-dinitroindolin-4-yloxy)acetic acid (CDNI-GABA) depicted by the formula (IV), the method comprising:
(a) providing ethyl(indolin-4-yloxy)acetate

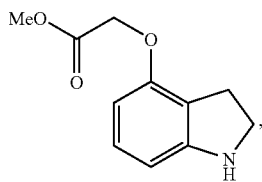
(X)

compound 2b in FIG. 2
(b) providing protected GABA

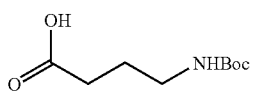
(XI)

(c) coupling ethyl(indolin-4-yloxy)acetate to protected GABA to form methyl {1-[4-(tert-butoxycarbonylamino) butanoyl]indolin-4-yloxy}acetate

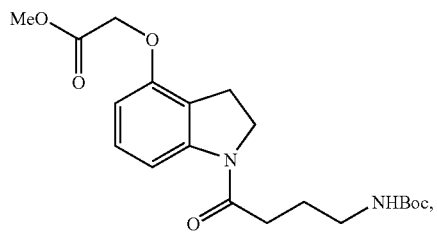
(XII)

compound 10 in FIG. 2
(d) treating methyl {1-[4-(tert-butoxycarbonylamino)butanoyl]indolin-4-yloxy}acetate with a base to give (compound 11) 1-[4-(tert-Butoxycarbonylamino)butanoyl]indolin-4-yloxy}acetic acid (5-CNI-GABA)

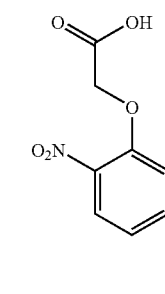
(VII)

compound 11 in FIG. 2
(e) mono-nitrating 1-[4-(tert-Butoxycarbonylamino)butanoyl]indolin-4-yloxy}acetic acid with about 1 equivalent of at least one of $NaNO_2$, $LiNO_3$, $KNO_3$, $CsNO_3$, $PF_6NO_2$, $CF_3SO_3NO_2$, $BF_4NO_3$ to form (1-[4-aminobutanoyl]-5-nitroindolin-4-yloxy)acetic acid and 1-[4-aminobutanoyl]-7-nitroindolin-4-yloxy)acetic acid

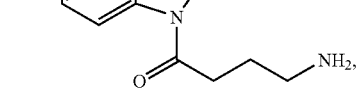
(VIII)

compound 12 in FIG. 2

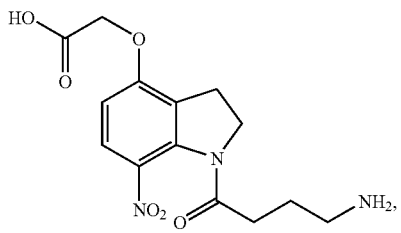

(IX)

compound 13 in FIG. 2

(f) separating (1-[4-aminobutanoyl]-5-nitroindolin-4-yloxy) acetic acid and 1-[4-aminobutanoyl]-7-nitroindolin-4-yloxy)acetic acid;

(g) treating (1-[4-aminobutanoyl]-5-nitroindolin-4-yloxy) acetic acid with a nitronium ion source to obtain (1-[4-aminobutanoyl]-5,7-dinitroindolin-4-yloxy)acetic acid.

In certain embodiments, the caged compound (1-[4-aminobutanoyl]-5,7-dinitroindolin-4-yloxy)acetic acid (CDNI-GABA) is obtained in about 5 to about 7% overall yield starting from ethyl(indolin-4-yloxy)acetate.

In a fourth aspect, the invention comprises a method of making a caged compound {1-[(4S)-(4-amino-4-carbonxybutanoyl]-5,7-dinitroindolin-4-yloxy}acetic acid depicted by the formula (III), the method comprising:

(a) providing 4-hydroindole;

(b) alkylating a phenol group in 4-hydroindole followed by reducing of the indole to give methyl(indolin-4-yloxy)acetate;

(c) providing a protected L-glutamate;

(d) coupling methyl(indolin-4-yloxy)acetate to the protected L-glutamate to provide ethyl {1-[4S-(4-tert-Butoxycarbonyl)-4-(tert-butoxycarbonylamino)butanoyl]indolin-4-yloxy}acetate;

(e) nitration to provide ethyl {1-[4S-(4-tert-butoxycarbonyl)-4-(tert-butoxycarbonylamino)butanoyl]-7-nitroindolin-4-yloxy}acetate;

(f) nitration to provide ethyl {1-[4S-(4-tert-butoxycarbonyl)-4-(tert-butoxycarbonylamino)butanoyl]-5,7-dinitroindolin-4-yloxy}acetate;

(g) base de-esterification to provide {1-[4S-(4-tert-butoxycarbonyl)-4-(tert-butoxycarbonylamino)butanoyl]indolin-4-yloxy}acetic acid;

(h) nitration to provide {1-[(4S)-(4-amino-4-carbonxybutanoyl]-5-nitroindolin-4-yloxy}acetic acid; and (i) nitration to provide {1-[(4S)-(4-amino-4-carbonxybutanoyl]-5,7-dinitroindolin-4-yloxy}acetic acid.

In certain embodiments, the caged compound is obtained in a yield of from about 25% to about 28%.

In a fifth aspect, the invention comprises a photolabile compound selected from the table:

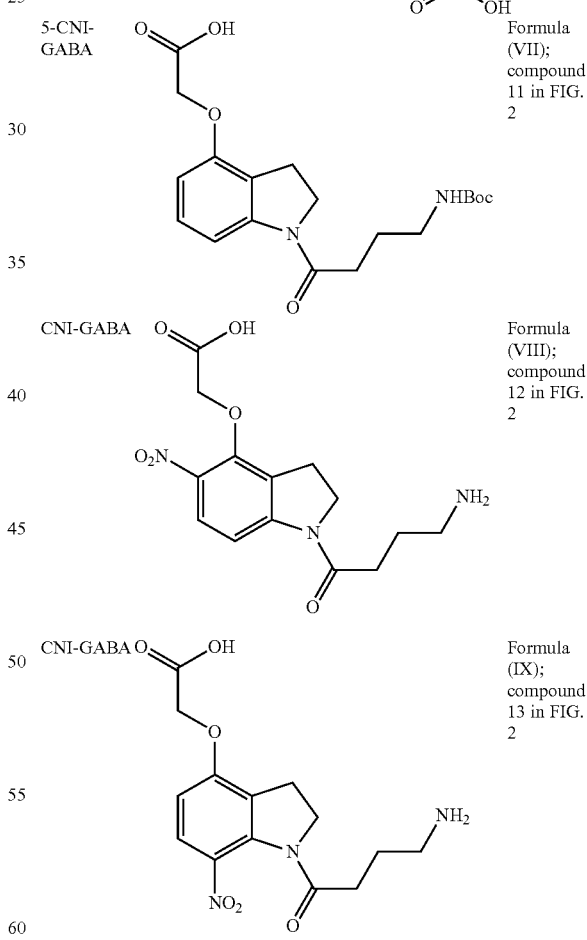

The present invention relates to photolabile or photoreleasable compounds comprising a caging moiety linked to an effector moiety, wherein the compounds are capable of releasing the effector moiety on irradiation, typically by flash irradiation with UV light. These compounds are particularly suitable for focal 2-photon uncaging The photoreleasable compounds can therefore be used to deliver effector moieties such as carboxylic acids, preferably, neuroactive amino acids to sites where their activity is required. In preferred embodiments of the invention, the caging moiety is based on 4-carboxymethoxy-5,7-dinitroinlinyl and substituted derivatives thereof.

Now with the development of carboxydinitroindolines as novel caging chromophores, much more photoreactive caged transmitters have become available. CDNI-Glu will permit much lower energies to be used for long-term mapping experiments, significantly extending the life of the stimulated cells, given access to a whole new range of biological hypotheses. CDNI-GABA (and CNI-GABA) are the first really useful caged GABAs that undergo photolysis so as to mimic biological activation of inhibitory receptors, thus they are completely new addition to the technological arsenal for biologists.

Abbreviations:
CDNI: 4-carboxymethoxy-5,7-dinitroinlinyl.
CNI: 4-carboxymethoxy-7-nitroinlinyl
MDNI: 4-methoxy-5,7-dinitroinlinyl
MNI: 4-methoxy-7-nitroinlinyl
GLU: glutamate
GABA: gamma-aminobutyric acid
CDNI-Glu: 4-carboxymethoxy-5,7-dinitroinlinylglutamate
CDNI-GABA: 4-carboxymethoxy-5,7-dinitroinlinyl-gamma-aminobutyric acid
MDNI-Glu: 4-methoxy-5,7-dinitroinlinylglutamate
CNI-Glu: 4-carboxymethoxy-7-nitroinlinylglutamate
CNI-GABA: 4-carboxymethoxy-7-nitroinlinyl-gamma-aminobutyric acid
AMPA: alpha-amino-3-hydroxy-5-methyl-4-isoxazolepropionic acid
TFA: trifluoroacetic acid

DETAILED DESCRIPTION OF PREFERRED EMBODIMENTS OF THE INVENTION

Caging Moiety/Chromophore

Figure 1:
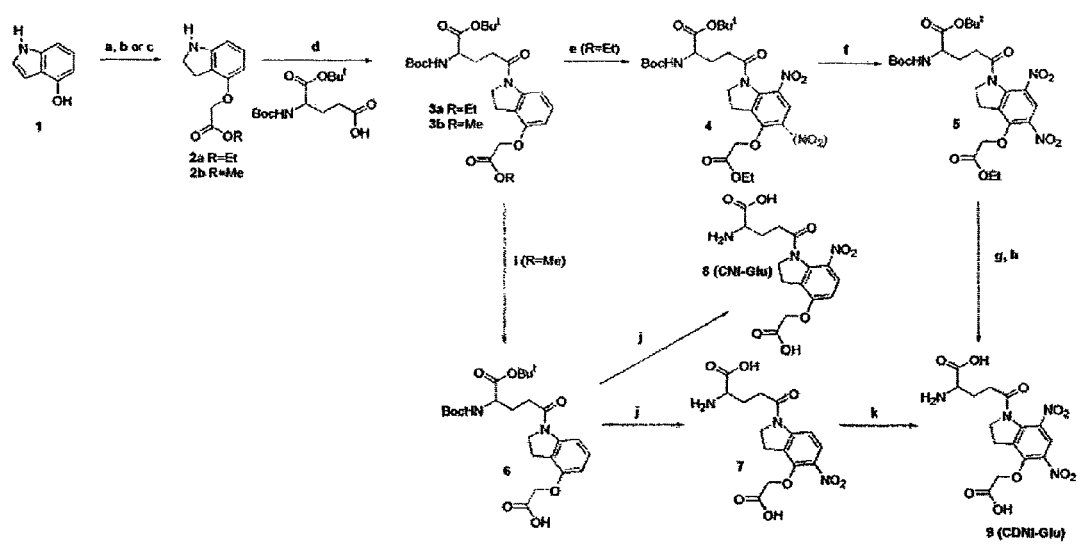
FIG. 1 is a scheme depicting synthesis of CDNI-caged glutamate.

The term "caging moiety" as used herein means a photosensitive moiety capable of caging a molecule of interest and releasing it upon illumination. The term "caging moiety" is used herein interchangeably with the term "chromophore."

Dinitroindolinyl Based Caging Moiety/Chromophore

In one aspect, the invention is a new dinitroindolinyl based caging moiety that is soluble in water or physiological buffer represented by the following structural formula:

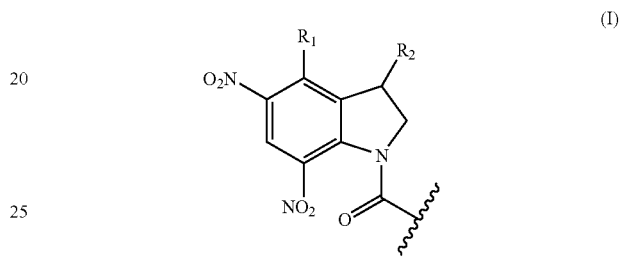

wherein $R_1$ is H, $O(CH_2)_nCO_2H$, $O(CH_2)_nOPO(OH)_2$, $O(CH_2)_nOSO_2(OH)$, $O(CH_2)_nC(O)NR_3$, $(CH_2)_nCO_2H$, $(CH_2)_nOPO(OH)_2$, $(CH_2)_nOSO_2(OH)$, $(CH_2)_nC(O)NR_3$, $C_{1-10}$ alkyl or substituted alkyl, $O(CH_2)_n$—Y, $N(COZ)$ $(CH_2)_mY$, or $N[(CH_2)_mQ][(CH_2)_nY]$, provided that $R_1$ is not OMe, $R_2$ is H, $(CH_2)_nCO_2H$, $(CH_2)_nOPO(OH)_2$, $(CH_2)_n$ $OSO_2(OH)$, $(CH_2)_nC(O)NR_3$ or $(CH)_nN(R_3)_2$, $R_3$ is H, Me, or Et, n and m are independently from 1 to 10, preferably n is from 1 to 5, Q and Y are independently selected from H, $CO_2H$ or salts thereof, or $OPO_3^{2-}$, and Z is H, $C_{1-10}$ alkyl or substituted alkyl.

Effector Moiety (X)

An effector moiety (X) can be selected from carboxylic acids or carboxylic acid like substances. Exemplary carboxylic acids include amino acids. Neuroactive aminoacids are preferred. Most preferred are L-glutamate (GLU), γ-aminobutyric acid (GABA), D-aspartate, and glycine.

The term "carboxylic acid-like substances" as used herein includes carbamates and ureas, which will be chemically protected alcohols and amines. Exemplary carboxylic acid-like substances include carbamoylcholine and adenosine.

Dinitroindolinyl Based Caged Photolabile Compounds

In another aspect, the invention is a dinitroindolinyl based caged photolabile compound comprising a dinitroindolinyl caging moiety (I) (a chromophore) covalently linked to an effector moiety (X) as depicted by the formula (II) below:

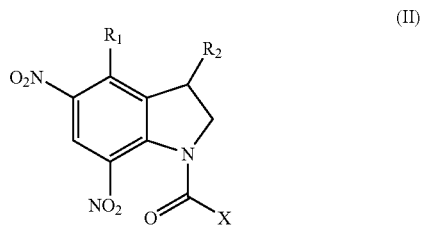

wherein X is a carboxylic acid, $R_1$ is $O(CH_2)_nCO_2H$, $O(CH_2)_nOPO(OH)_2$, $O(CH_2)_nOSO_2(OH)$, $O(CH_2)_nC(O)NR_3$, $(CH_2)_nCO_2H$, $(CH_2)_nOPO(OH)_2$, $(CH_2)_nOSO_2(OH)$, $(CH_2)_nC(O)NR_3$, $C_{1-10}$ alkyl or substituted alkyl, $O(CH_2)_n$-M, $N(COZ)(CH_2)_mY$, or $N[(CH_2)_mQ][(CH_2)_nY]$, $R_2$ is H, $(CH_2)_nCO_2H$, $(CH_2)_nOPO(OH)_2$, $(CH_2)_nOSO_2(OH)$, $(CH_2)_nC(O)NR_3$ or $(CH)_nN(R_3)_2$, $R_3$ is H, Me or Et, n and m are independently from 1 to 10, Q and Y are independently selected from H, $CO_2H$ or salts thereof, or $OPO_3^{2-}$, M is selected from $CO_2H$ or salts thereof, or $OPO_3^{2-}$, Z is H, $C_{1-10}$ alkyl or substituted alkyl.

Preferred examples of dinitroindolinyl based caged photolabile compounds include CDNI-glutamate and CDNI-GABA as depicted below by formulas (III) and (IV):

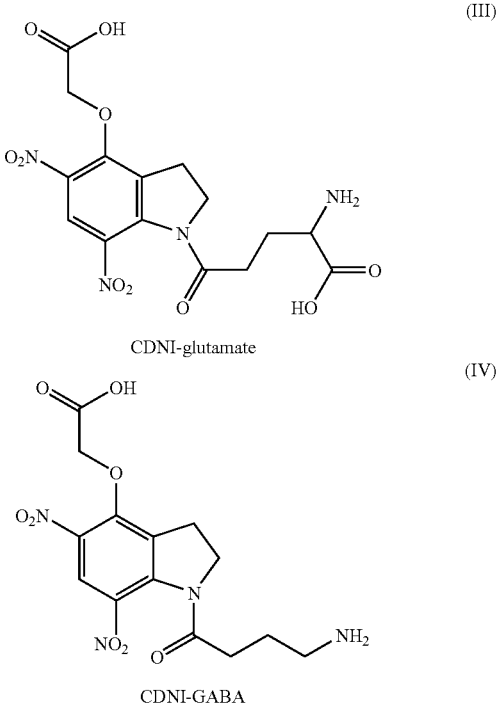

CDNI-Glu and CNDI-GABA are preferred examples of new caged compounds.

Direct comparison of 2-photon uncaging of MNI-Glu and CNDI-Glu on the same neuron shows that CNDI-Glu is about 12-16-times more photosensitive than the MNI-Glu. Given the power-squared law for 2-photon excitation (Denk, et al., 1990), this implies that the new chromophore is about 140-250 higher action cross-section for 2-photon uncaging, defined by Denk et al. (1990).

The improvement of the 5-nitro substituents upon GABA release can be seen by comparing the powers and concentrations required for uncaging of CNI-GABA and CDNI-GABA (MNI-GABA is not soluble enough for uncaging). In order to evoke currents with CNI-GABA 20 mW for 2 ms and 10 mM must be used, whereas with CDNI-GABA only 4 mW and 0.5 mM are required. Thus, for GABA receptors on CA1 neurons, CDNI-GABA is about-5-10 times more effective. The effectiveness of CDNI-GABA is believed to be an important asset because high concentrations of the cages block GABA receptor before uncaging. Advantageously, due to high 2P action cross section, CDNI-GABA can be used in a smaller amount than known cages such that it is not blocking before uncaging and therefore one can efficiently activate GABA receptors with non-phototoxic doses of uncaging energy. The inventor discovered that if the same neuron is stimulated with 20 mW and 2 ms pulses repetitively 10 times, photodamage can be detected as seen by decrease in the current response.

Synthesis of Caged Photolabile Compounds

Inventor had discovered that making dinitro based caged photolabile compounds of the invention based on a synthesis previously described (Fedoryak, et al., 2005), provided a very small yield (0.012%).

When organic chemists make molecules, they like to use organic solvents to purify them with silica gel chromatography. Thus, the molecule must be uncharged, else they cannot be purified. Thus, molecules that are intended to be water soluble must carry chemical protecting groups to mask the charges (Fedoryak, et al., 2005). Using this route for preparation of CDNI-glu, the inventor had observed that the molecule underwent multiple reactions to give a horrible complex mixture of no practical use. The inventor had found that in order to make CDNI-glu, the protecting groups would have to be removed first to allow the second nitro group to preferentially attack the 5-position of the indoline.

Figure 2:
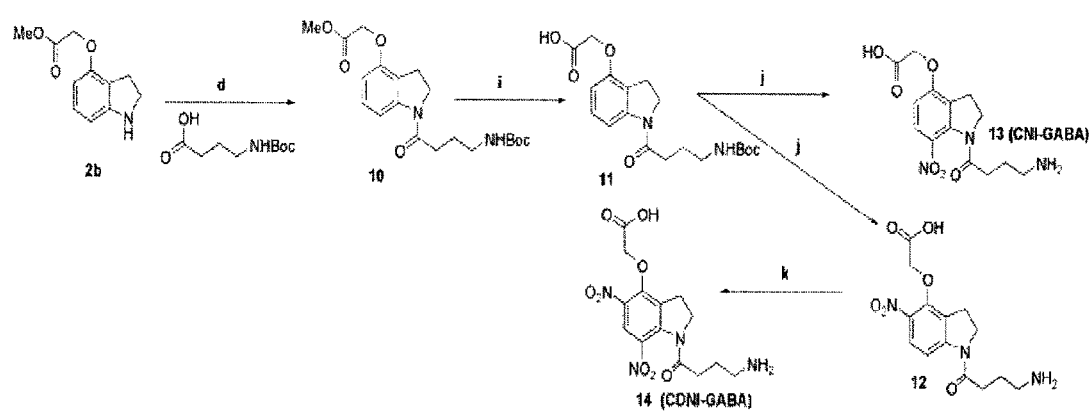
FIG. 2 is a scheme depicting synthesis of CDNI-caged GABA.

Examples of synthesis of caged photolabile compounds of the invention are shown in FIGS. 1 and 2.

FIG. 1 illustrated synthesis of CDNI-caged glutamate. Two related routes to CDNI-Glu were developed, both starting from commercially available 4-hydroindole 1. The shortest route starts with alkylation of the phenol with bromoethylacetate followed by reduction of the indole to give indoline 2a. Carbodiimide coupling of the commercially available protected L-glutamate and 2a gave 3a. Sequential dinitration of this compound under mild (claycop, step e) and stringent (fuming nitric acid, step f) gave fully protected CDNI-Glu, 5 (via compound 4). Treatment of 5 with LiOH then TFA gave CDNI-Glu in very modest and unsatisfactory overall yield from amidoester 3a. Introduction of the second nitro group is difficult (Fedoryak, et al., 2005) as the first nitro substituent decreases the electrophilic reactivity of the aromatic ring due to its strong electron withdrawing power. Harsh nitration conditions are required to force dinitration, and so compound 4 undergoes competing reactions, probably nitration of the BOC-protected amide. Thus, starting from 1 g of indole, only 1 mg of final product could be isolated, making this synthetic route impractical for production of useful quantities of CDNI-Glu (i.e. hundreds of milligrams). During our studies, an efficient five-step synthesis of compound 4b was published that required no column chromatography (Papageorgiou, et al., 2004). Deprotection of the methyl ester of 4b with NaOH gave acid 6 in 83% yield. Chemically efficient dinitration of 6 using various reagents proved as elusive as that of 4. Based upon this experience, it was determined that prior removal of the BOC and tert-butyl protecting groups might enable efficient dinitration under acidic conditions, as the amine would be protonated and consequently less likely to react. This proved to be the case. Thus, acid 6 was dissolved in TFA at RT for 3 h (BOC deprotection was relatively slow, and was monitored by HPLC), then 1.2 equivalents of $NaNO_3$ was added to this solution as a solid at RT; mononitration was essentially instantaneous, as shown by HPLC. The resulting equal mixture of 5-nitro derivatives 7 and 7-nitro derivatives 8, CNI-Glu were separated by HPLC in 80% yield. Attempts to nitrate the crude mixture failed almost completely, giving complex mixtures of multi-nitrated products. The 5-nitro isomer 7 was then nitrated under similar conditions to 6, except 20 equivalents of $NaNO_3$ were used, and the reaction mixture was stirred vigorously at RT for 4-6 days. The extent of reaction was monitored by HPLC, as deleterious side-reactions produced a complex mixture of products if care was not taken. CDNI-Glu (compound 9) was isolated by HPLC in 25% yield from 5-nitro compound 7. A similar yield of CDNI-Glu was achieved when pure CNI-Glu (8) was nitrated under similar conditions.

Chemically efficient production of CDNI-Glu requires the synthesis of pure deprotected mono-nitro amino acids 7 and 8. Removal of all protecting groups was required for addition of the all-important second nitro group. Thus, using the new dinitration route, CDNI-Glu was synthesized in 6.9% overall yield from indole 1, whereas the yield was only 0.032% when using the previously described route in the synthesis of MDNI-Glu (Fedoryak, et al., 2005).

Figure 3:
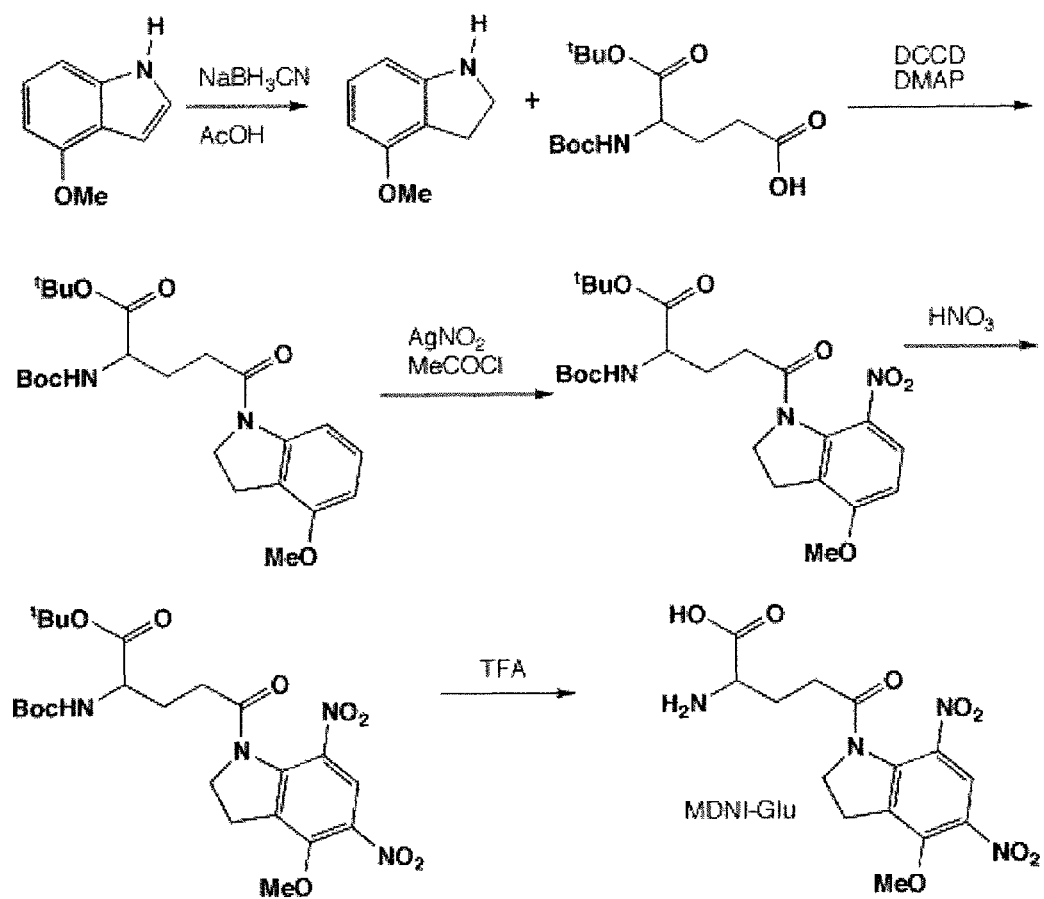
FIG. 3 is a scheme depicting synthesis MDNI-glu (see Fedoryak et. al., "Synthesis of a caged glutamate for efficient one and two-photon photorelease on living cells." Chem. Comm. (2005) 3664).

The synthesis of CDNI-Glu by the method of the invention is important for at least two reasons: (1) it is chemically much more efficient than the previous MDNI-Glu synthesis (Fedoryak, et al., 2005) (FIG. 3) at creating the photochemically desirable dinitro ring substituents, and (2) the pendant carboxylate creates additional charge at physiological pH enabling smooth solubilization of useful concentrations of CDNI-Glu. The inventor found that addition of the extra nitro group at the 5-position made MDNI-Glu impractical for day-to-day use in physiology as only dilute solutions of 1 mM could be made, though in practice, it was found that 2-photon uncaging of such solutions did not evoke any current signals from hippocampal neurons, leading us to suspect that MDNI-Glu was even less soluble in physiological buffer on brain slices. Furthermore, MDNI-Glu was observed to precipitate in buffer when frozen, and would not re-dissolve at room temperature. Advantageously, inventor had discovered that addition of the negative charge with CDNI-Glu solves both of these problems Irradiation of solutions CDNI-Glu and MNI-Glu at pH 7.4 showed that the quantum yield of photolysis of CDNI-Glu was about 0.5, which is six times higher than that in case of MNI-Glu (Papageorgiou & Corrie 2000). NMR analysis of the reaction mixture revealed that L-glutamate was released essentially quantitatively from CDNI-Glu. Furthermore, NMR analysis of a photolysis solution of 7, CNI-Glu and CDNI-Glu showed that during the time required for complete photolysis of CDNI-Glu only about 10% of the CNI-Glu was photolyzed. Comparative irradiation of MNI-Glu and CNI-Glu revealed that the quantum yield of photolysis of the latter was about 0.1. The data imply that the quantum yield for release of L-glutamate from CDNI-Glu was about 0.5.

Biological evaluation of the photolytic efficacy of CNDI-Glu in acutely isolated brain slices was consistent with the high quantum yield of glutamate uncaging. Sequential, alternating application and uncaging of solutions of MNI-Glu and CDNI-Glu to the same CA1 pyramidal neuron produced AMPA-receptor currents that were five-times larger for CDNI-Glu than that for MNI-Glu. Importantly, the rise- and decay-times of the evoked currents were similar for both cages. These data suggest that CDNI-Glu is biologically inert, as MNI-Glu, which has been evaluated by many laboratories (Matsuzaki, et al., 2001; Canepari, et al., 2001; Huang, et al., 2005; Bernardinelli, et al., 2005; Shepherd & Svoboda, 2005; Shoham, et al., 2005; Bloodgood & Sabatini, 2005 Smith, et al., 2003; Matsuzaki, et al., 2004; Noguchi, et al., 2005; Carter & Sabatini, 2004; Sobczyk, 2005; Gasparini & Magee, 2006; Losonczyi & Magee, 2006). Since the same laser energy evoked a larger current for CDNI-Glu, but with the same kinetics as MNI-Glu, the new cage did not interfere with glutamate activation of AMPA receptors.

FIG. 2 illustrated synthesis of CDNI-caged GABA. The synthesis of CDNI-GABA was similar to CDNI-Glu (FIG. 1), except that a different amino acid, GABA, was applied. Using compound 2b (Papageorgiou, et al., 2004) from the caged glutamate synthesis, the protected GABA was coupled to give 10.

The methyl ester was cleaved with base (non-limiting examples of suitable bases include LiOH, $(Bu)_4NOH$ or NaOH) to give 11, which was mono-nitrated with about 1 equivalent of sodium nitrate to give 12 and 13. The BOC protecting group was removed under the nitration conditions (TFA). Compounds 12 and 13 were separated by HPLC. The 5-Nitro isomer was then nitrated second time to give 14 in 29% yield.

Photolysis of solutions of CNI-GABA and CDNI-GABA at pH 7.4 using a continuous-wave mercury arc lamp showed that the former was photolyzed about 10% and the latter 700% faster than MNI-Glu, implying quantum yields of photolysis of 0.1 and 0.6 respectively. The extent of photolysis was measured either by HPLC (with inosine as the internal standard), or using the inherent changes in the UV-visible absorption spectra of the chromophores (FIGS. 4A-4D).

Figure 4:
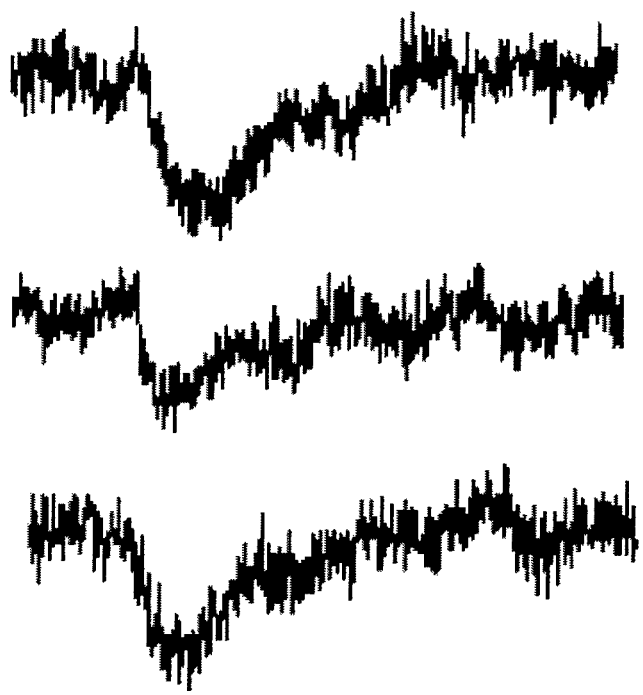
FIGS. 4A-4D are current traces demonstrating comparison of AMPA receptor currents evoked by 2-photon uncaging of CDNI-GABA, MNI-Glu and CNI-GABA on neurons in acutely isolated brain slices. (4A) Normal GABA-currents from spontaneous release of GABA at inhibitory synapses (so-called miniature inhibitory post-synaptic currents, or mIPSC) from hippocampal CA1 neurons from P18 rats, (4B) 2-photon evoked IPSC using 0.55 mM CDNI-GABA, 4 mW 720 nm light, for 1 ms irradiation (shutter) time, (4C) 2-photon uncaging of MNI-Glu (10 mM, 20 mW, 2 ms) on a different neuron, (4D) 2-photon uncaging of CNI-GABA on the same neuron as MNI-Glu under the same conditions.
Figure 4B:
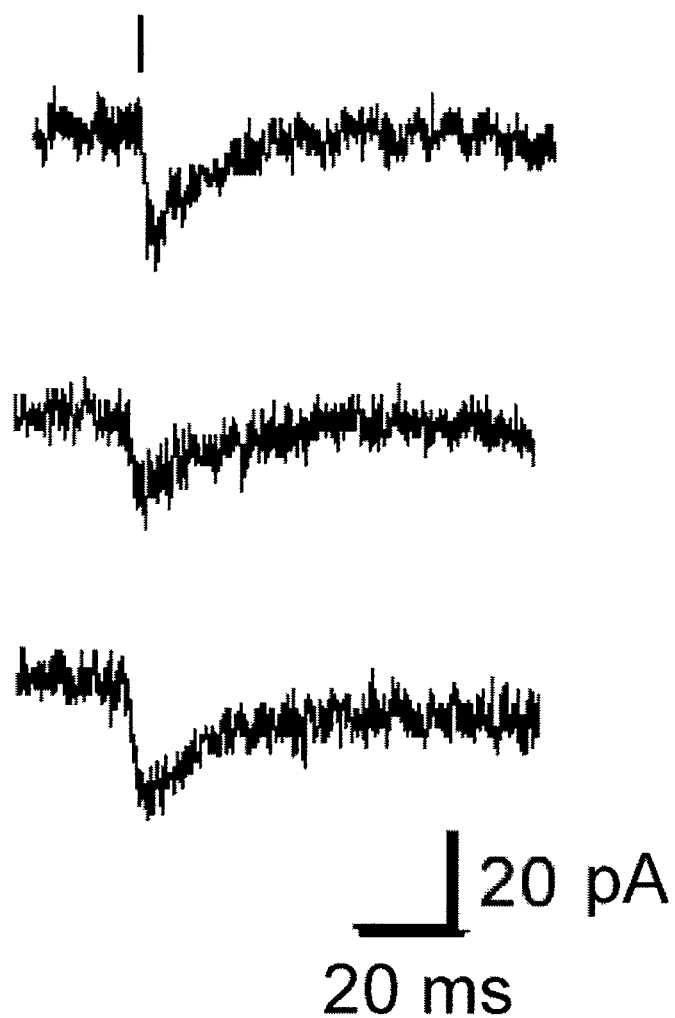
Figure 4C:
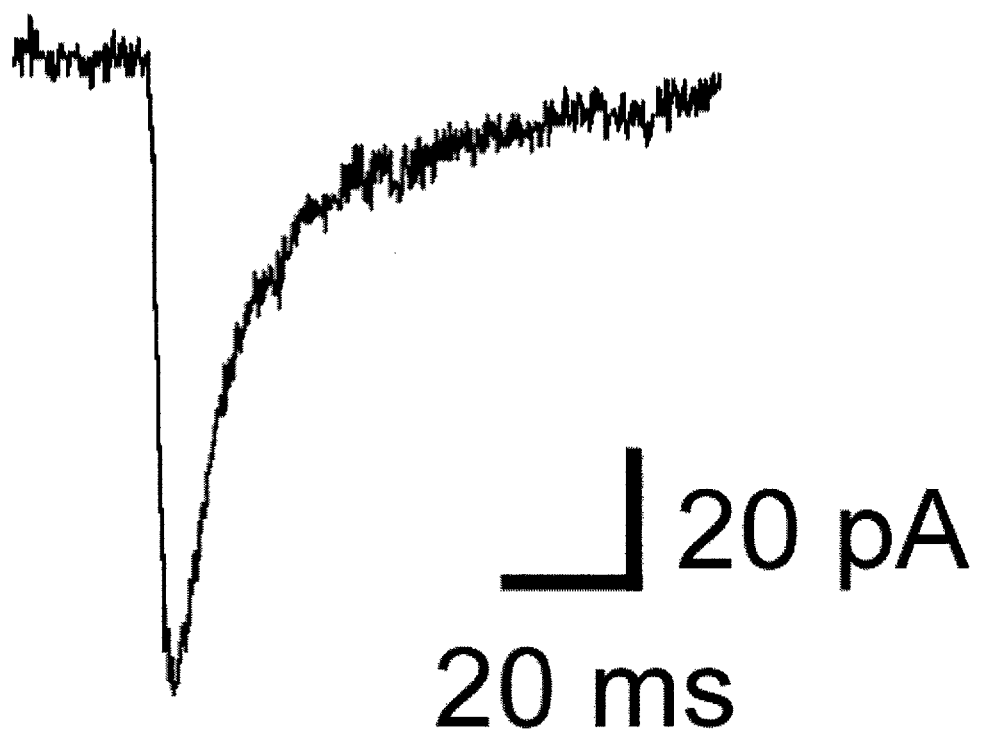
Figure 4D:
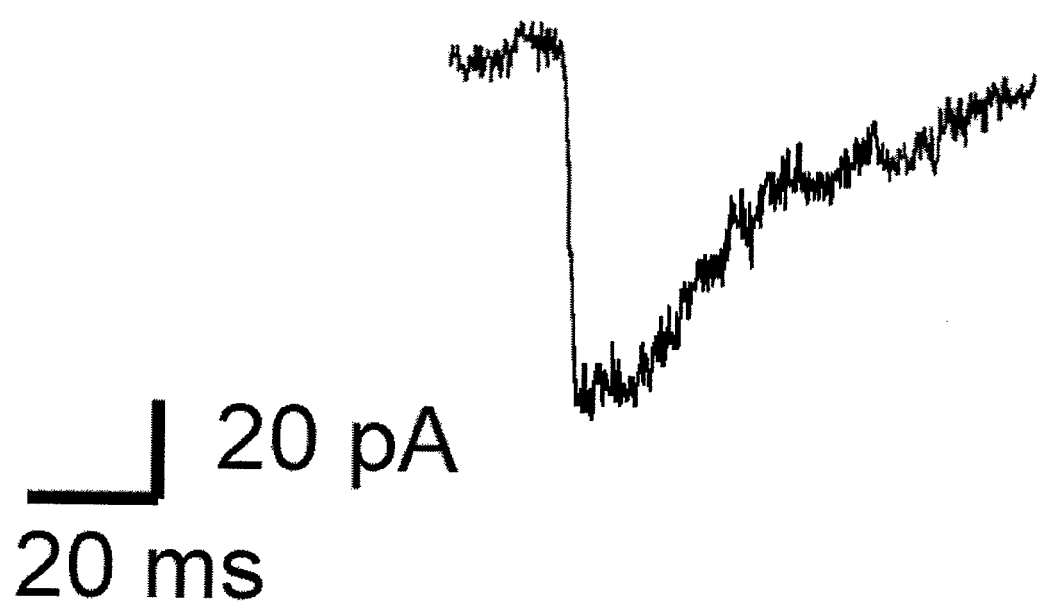

Using 2-photon uncaging of CNI-GABA, rapid inhibitory post-synaptic currents (IPSC) was evoked that have a similar rise-time to the excitatory post-synaptic currents (EPSC) evoked by photolysis of MNI-Glu on the same neuron (compare FIGS. 4C and 4D).

Using CDNI-GABA, it was found that much lower concentrations of the caged compound could be used with lower energies than CNI-GABA (0.55 mM vs. 10 mM; 4 mW vs. 20 mW respectively), reflecting the photochemical efficiency of release of GABA. This allows for long-term mapping of receptors at low energies, which is a highly desirable feature for neuroscience experiments, since light is always eventually phototoxic to some extent.

The new caged GABAs greatly extend the ubiquity and impact of nitroindoline cages. The properties of these new caged transmitters are summarized in Table 1 below.

TABLE 1

Basic photochemical properties of new caged transmitters

| Cage | ε | φ | ε · φ | δ (relative) |
|---|---|---|---|---|
| MNI-Glu | 4,300 | 0.085 | 366 | 1 |
| CDNI-Glu | 8,600 | 0.5 | 4,300 | 5-10 |
| CNI-Glu | 4,300 | 0.1 | 430 | 1 |
| CNI-GABA | 4,300 | 0.1 | 430 | 1 |
| CDNI-GABA | 8,600 | 0.6 | 5160 | 5-10 |

Symbols: ε, molar extinction coefficient $(M^{-1} cm^{-1})$; φ, quantum yield; δ, two-photon action cross section $(10^{-50} cm^4 s/photon)$.

Synthesis of CDNI-Glu will now be described in detail.
Ethyl(indolin-4-yloxy)acetate 2a.

To a solution of commercially available 4-hydroindole (compound 1, 0.226 g, 1.7 mmol) and potassium carbonate (0.704 g, 5.1 mmol) in acetone was added ethyl bromoacetate (0.3 mL, 2.6 mmol). The reaction mixture was stirred at RT for 18 h, and then filtered. The solvent was removed and the green oil was purified by flash chromatography [hexanes-ethyl acetate (4:1)] to give ethyl(indol-4-yloxy)acetate. NMR: δ (300 MHz, $CDCl_3$) 8.2 (br s, 1H), 7.13 (dd, J=5.6, 2.3 Hz, 1H), 7.1-7.06 (m, 2H), 6.73 (t, J=2.4 Hz), 6.43 (dd, J=5.9, 2.7 Hz, 1H), 4.78 (s, 2H), 4.28 (q, J=7.4 Hz, 2H), 1.31 (t, J=7.4 Hz, 3H). To a solution of this indole in acetic acid (10 mL) was added sodium cyanoborohydride (0.302 g, 4.8 mmol) as a solid. The reaction mixture was stirred at RT for 18 h, then neutralized with aqueous sodium bicarbonate and extracted with diethyl ether. The solvent was removed to give compound 2a (0.308 g, 88% yield) as a colorless oil. NMR: δ (300 MHz, CDCl$_3$) 6.98 (d, J=7.9 Hz, 1H), 6.39 (t, J=7.9 Hz, 1H), 6.18 (d, J=7.9 Hz, 1H), 4.62 (s, 2H), 4.28 (q, J=7.0, Hz, 2H), 3.58 (t, J=8.4 Hz, 2H), 3.07 (t, J=8.4 Hz, 2H), 1.30 (t, J=7.0 Hz, 3H).

Ethyl {1-[4S-(4-tert-Butoxycarbonyl)-4-(tert-butoxycarbonylamino)butanoyl]indolin-4-yloxy}acetate 3a. A solution of 2a (0.84 g, 3.8 mmol), dicyclohexylcarbodiimide (1.01 g, 4.9 mmol), N—BOC-L-glutamate acid γ-tert-butyl ester (1.49 g, 4.9 mmol) and dimethylaminopyridine (0.6 g, 4.9 mmol) in dichloromethane were stirred for 18 h. The precipitate was filtered, and the filtrate washed with saturated sodium bicarbonate, 0.1 N HCl, and brine. The organic solvent was evaporated and the product isolated by flash chromatography to give 3a (1.43 g, 74% yield). NMR: □ (300 MHz, CDCl$_3$) 7.86 (d, J=8.1 Hz, 1H), 7.13 (t, J=8.1 Hz, 1H), 6.43 (d, J=8.1 Hz, 1H), 5.23 (br d, J=8.8 Hz 1H), 4.64 (s, 2H), 4.25 (q, J=7.1 Hz, 2H), 4.05 (t, J=8.0 Hz, 2H), 3.19 (t, J=8.0 Hz, 2H), 2.6-2.4 (m, 2H), 2.35-2.20 (m, 1H), 2.1-1.9 (m, 1H), 1.46 (s, 9H), 1.42 (s, 9H), 1.29 (t, J=8.0 Hz, 3H).

Ethyl {1-[4S-(4-tert-Butoxycarbonyl)-4-(tert-butoxycarbonylamino)butanoyl]-7-nitroindolin-4-yloxy}acetate 4. To a solution of 3a (1.0 g, 1.97 mmol) in carbon tetrachloride (15 mL) and acetic anhydride (7.5 mL) was added claycop (0.95 g). The reaction mixture was stirred at RT for 18 h, then, more claycop was added and after 5 h the reaction mixture was filtered, washed with sodium bicarbonate solution, dried over magnesium sulphate, and the solvent removed to give a dark orange oil. Flash chromatography [ethyl acetate-hexanes, 35:65] gave 4 (0.278 g, 26% yield) plus recovered starting material (0.287 g, 19%). NMR (7-isomer): δ (300 MHz, CDCl$_3$) 7.69 (d, J=12.1 Hz, 1H), 6.49 (d, J=121. Hz, 1H), 5.2 (br d, J=8.8 Hz 1H), 4.71 (s, 2H), 4.26 (q, J=7.0 Hz, 2H), 4.22 (t, J=8.2 Hz), 2.7-2.4 (m, 2H), 2.4-2.2 (m, 1H), (2.1-1.9 (m, 1H), 1.46 (s, 9H), 1.43 (s, (H), 1.30 (t, J=7.0 Hz, 3H).

Ethyl {1-[4S-(4-tert-butoxycarbonyl)-4-(tert-butoxycarbonylamino)butanoyl]-5,7-dinitroindolin-4-yloxy}acetate 5. To a solution of 4 in (0.05 g, 0.09 mmol) in acetic anhydride (2 mL) was added nitric acid (1.8 mmol). After 18 h at RT the reaction mixture was poured into a sodium hydroxide solution and extracted with ethyl acetate. The orange solid was purified by flash chromatography [ethyl acetate-hexanes, 2:3] to give a 1:1 mixture of 6 and 4 with other components (total weight isolated 16 mg, of which ca. 25% was 6). NMR: δ (300 MHz, CDCl$_3$) 8.21 (s, 1H), 5.1 (br s, 1H), 4.70 (s, 2H), 4.24 (t, J=7.0 Hz, 2H), 4.15 (t, J=8.0 Hz, 2H), 3.43 (t, J=8.0 Hz, 2H), 2.8-2.6 (m, 2H), 1.5 (s, 9H0, 1.4 (s, 9H), 1.27 (t, J=7.0 Hz, 3H).

{1-[4S-(4-tert-Butoxycarbonyl)-4-(tert-butoxycarbonylamino)butanoyl]indolin-4-yloxy}acetic acid 6. To a solution of 3b (4.0 g, 8.1 mmol) in methanol was added sodium hydroxide (12.2 mmol, 12.2 mL of a 1N solution). After 1 h at RT, the RM was neutralized with citric acid (12 mL of a 1N solution), and the methanol was removed by rotary evaporation. The aqueous phase was extracted with ethyl acetate, and the organic solvent was removed to give essential pure compound 6 (2.63 g, 68% yield). NMR: δ (300 MHz, CDCl$_3$) 7.84 (d, J=8.0 Hz, 1H), 7.12 (t, J=8.0 Hz, 1H), 6.45 (d, J=8.0 Hz, 1H), 5.33 (br d, J=7.9 Hz, 1H), 4.62 (s, 2H), 3.98 (m, 2H) 3.2-2.95 (M, 2H), 2.6-2.4 (m, 2H), 2.4-1.9 (m, 2H), 1.47 (s, 18H).

{1-[(4S)-(4-Amino-4-carbonxybutanoyl]-5-nitroindolin-4-yloxy}acetic acid 7. A solution of 6 in TFA (30 mL) was stirred for 3 h, then sodium nitrate (0.723 g, 8.5 mmol) was added as a solid at RT. HPLC analysis of the RM after 75 and 135 min indicated that about 8% of 6 remained, therefore more sodium nitrate was added (0.125 g) to complete the nitration. HPLC showed no SM remaining and 8 (CNI-Glu) and 7 as the only products. The TFA was removed with a stream of nitrogen and then a vacuum pump (0.01 torr) for 18 h (NMR of the reaction mixture showed equal amounts the two products). The reaction mixture was dissolved in water, passed through a 0.45 filter and the two products were separated by preparative HPLC on an Alltech Altima C$_{18}$ column (22×250 mm) using isocratic elution (20% acetonitrile, 0.1% TFA, 10 mL/min). CNI-Glu 8 eluted at 11 min and 7 at 15 min. NMR: δ (300 MHz, MeOD) compound 7: 8.04 (d, J=8.5 Hz, 1H), 7.88 (d, J=7.9 Hz, 1H), 4.69, (s, 2H), 4.23 (t, J=8.8 Hz, 2H), 4.11 (t, J=6.7 Hz, 1H), 3.35 (t, J=7.9 Hz, 2H), 2.81 (t, J=6.9 Hz, 2H), 2.30 (m, 2H).

{1-[(4S)-(4-Amino-4-carbonxybutanoyl]-5,7-dinitroindolin-4-yloxy}acetic acid (compound 9, FIG. 1) (CDNI-Glu). To a solution of 7 (36 mg, 0.098 mmol) in TFA was added sodium nitrate (0.14 g, 1.6 mmol), and the slurry was stirred at RT for 6 days. The solvent was removed under a stream of nitrogen and then under high vacuum. The reaction mixture was dissolved in water and purified by HPLC (as above for CNI-Glu) to give CDNI-Glu (10 mg, 25% yield). NMR: δ (300 MHz, D$_2$O) 8.53 (s, 1H), 4.81 (s, 2H), 4.43 (t, J=8.2 Hz, 2H), 3.96 (t, J=6.9 Hz, 1H), 3.39 (t, J=7.8 Hz, 2H), 2.88 (t, J=7.1 Hz, 2H), 2.25 (q, J=7.0 Hz, 2H).

Synthesis of CDNI-GABA.
Synthesis of Compound 2b.
4-Acetoxy-1-acetylindoline. A solution of 4-hydroxyindole (6.66 g, 50 mmol) in acetic acid (250 mL) was treated with NaBH3CN (9.42 g, 150 mmol) over 0.5 h, keeping the temperature at <15 C. The mixture was then stirred at room temperature for 1 h and water (5 mL) was added and the solvent evaporated. The residue was dissolved in EtOAc (150 mL) and washed with saturated aq. NaHCO3 and brine, dried and evaporated to give 4-hydroxyindoline as pale crystals (6.76 g. 100%); 1H NMR (δ, CDCl$_3$ DMSO-d6): 6.82 (1H, t, J=8 Hz), 6.20 (1H, d, J=8 Hz), 6.16 (1H, d, J=8 Hz), 3.52 (2H, t, J=8 Hz) and 2.90 (2H, d, J=8 Hz). The crude indoline was dissolved in a mixture of acetic acid (50 mL) and acetic anhydride (50 mL) and heated under reflux for 1 h. The solution was diluted with water (10 mL) and the solvents evaporated. The residue was dissolved in EtOAc (150 mL) and washed with saturated aq. NaHCO3 and brine, dried and evaporated to give 4-acetoxy-1-acetylindoline as pale crystals (9.01 g, 82%), NMR (δ, 90 MHz): 8.07 (1H, d, J=8 Hz), 7.19 (1H, t, J=8 Hz), 6.72 (1H, d, J=8 Hz), 4.05 (2H, t, J=8 Hz), 3.03 (2H, t, J=8 Hz) 2.28 (3H, s) and 2.19 (3H, s).

1-Acetyl-4-hydroxyindoline. A solution of 4-acetoxy-1-acetylindoline (8.77 g, 40 mmol) in MeOH (250 mL) was treated with 2 M aq. NaOH (22 mL, 44 mmol), stirred at room temperature for 0.75 h, diluted with water (100 mL) and concentrated. The residue was acidified to pH 3 with 2 M aq. HCl and the precipitate was filtered, washed with water and dried under vacuum. The filtrate was extracted with EtOAc and the organic phase was washed with saturated aq. NaHCO3 and brine, dried and evaporated to give more solid. The combined solids were recrystallised (EtOAc) to give 17 as white crystals (5.75 g, 82%), NMR (δ, 90 CDCl$_3$ DMSO-d6): 9.10 (1H, br s), 7.57 (1H, d, J=8 Hz), 6.93 (1H, t, J=8 Hz), 6.48 (1H, d, J=8 Hz), 4.05 (2H, t, J=8 Hz), 3.04 (2H, t, J=8 Hz) and 2.16 (3H, s). Methyl (1-acetylindolin-4-yloxy)acetate. A suspension of K2CO3 (6.64 g, 48 mmol) in acetone (250 mL) was mixed with 1-acetyl-4-hydroxyindoline (5.67 g, 32 mmol). After 15 min, methyl bromoacetate (7.34 g, 48 mmol) was added and the mixture was heated under reflux for 4 h. The solid was filtered, washed with acetone and the filtrate was evaporated, to give methyl (1-acetylindolin-4-yloxy)acetate as white crystals (7.19 g, 90%), NMR (δ): 7.88 (1H, d, J=8 Hz), 7.14 (1H, t, J=8 Hz), 6.44 (1H, d, J=8 Hz), 4.66 (2H, s), 4.08 (2H, t, J=8.5 Hz), 3.79 (3H, s), 3.20 (2H, t, J=8.5 Hz) and 2.21 (s, 3H).

Methyl(indolin-4-yloxy)acetate (2b). A solution of methyl (1-acetylindolin-4-yloxy)acetate1 (2.74 g, 11 mmol) in a mixture of MeOH (230 mL), water (36 mL), and concentrated HCl (18 mL) was refluxed for 4 h. The solution was diluted with water (100 mL), concentrated to 200 mL, basified with solid $NaHCO_3$, and extracted with EtOAc (100 mL). The combined organic phases were washed with brine, dried, and evaporated to give methyl(indolin-4-yloxy)acetate (2b) (1.77 g, 77%) as pale crystals: NMR 6.92 (t, J) 7.5 Hz, 1H), 6.31 (d, J) 7.5 Hz, 1H), 6.12 (d, J) 7.5 Hz, 1H), 4.62 (s, 2H), 3.76 (s, 3H), 3.56 (t, J) 8 Hz, 2H), 3.05 (t, J) 8 Hz, 2H).

Methyl {1-[4-(tert-butoxycarbonylamino)butanoyl]indolin-4-yloxy}acetate 10. To a solution of 2b (0.84 g, 4.06 mmol) dicyclohexylcarbodiimide (0.927 g, 4.5 mmol), N—BOC-4-aminobutyric acid (0.914 g, 4.5 mmol) and dimethylaminopyridine (catalytic) in acetonitrile were stirred for 18 h. The reaction mixture was filtered and the solvent removed to give a dark brown liquid that was purified by flash chromatography [hexanes-ethyl acetate, (1:1)] to give 8 (0.994 g, 59 yield) and recovered 2b (0.182 g). NMR: δ (300 MHz, $CDCl_3$) 7.88 (d, J=8.0 Hz, 1H), 7.14 (t, J=8.0 Hz, 1H), 6.43 (d, J=8.0 Hz, 1H), 4.8 (br s, 1H), 4.67 (s, 2H), 4.08 (t, J=8.5 Hz, 2H), 3.80 (s, 3H), 3.26-3.17 (m, 4H), 2.47 (t, J=7.0 Hz, 2H), 1.93 (m, 2H).

1-[4-(text-Butoxycarbonylamino)butanoyl]indolin-4-yloxy}acetic acid 11. To a solution of 10 (0.99 g, 2.40 mmol) in methanol (50 mL) was added sodium hydroxide (3.6 mL of a 1N solution). After 3 h at RT citric acid (3.6 mL of a 1N solution) was added and the methanol was removed by rotary evaporation and the reaction mixture was extracted with ethyl acetate. The organic solvent was removed to give 11 (0.78 g, 77% yield) as a foamy light yellow solid. NMR (some peaks appear as rotamers): δ (300 MHz, $CDCl_3$) 7.86 (d, J=8.0 Hz, 1H), 7.13 (t, J=8.0 Hz, 1H), 6.46 (d, J=8.0 Hz, 1H), 4.84 (br s, 1H), 4.65/4.61 (s, 2H) 4.01 (br s, 2H), 3.22 (br s, 2H), 3.14/3.07 (br t, 2H), 2.6-2.4 (m, 2H), 2-1.8 (m, 2H), 1.49/1.42 (s, 9H).

(1-[4-Aminobutanoyl]-5/7-nitroindolin-4-yloxy)acetic acids 12/13 (CNI-GABA). A solution of 11 (0.78 g, 1.85 mmol) in TFA was stirred at RT for 3 h, then sodium nitrate (0.19 g, 2 mmol) was added as solid, and after 1 h at RT an additional amount of nitrate was added. HPLC showed no SM. The TFA was removed with a stream of nitrogen and then a vacuum pump (0.01 torr) for 18 h (NMR of the reaction mixture showed equal amounts the two products). The reaction mixture was dissolved in water, passed through a 0.45 filter and the two products were separated by preparative HPLC on an Alltech Altima $C_{18}$ column (22×250 mm) using isocratic elution (20% acetonitrile, 0.1% TFA, 10 mL/min). 13 (CNI-GABA) eluted at 15 min and 12 at 18 min. NMR: δ (300 MHz, MeOD) 10, 7.90 (d, J=8.9 Hz, 1H), 7.80 (d, J=8.9 Hz, 1H), 4.66 (s, 2H), 4.19 (t, J=8.5 Hz, 2H), 3.28 (t, J=8.0 Hz, 2H), 3.08 (t, J=7.0 Hz, 2H), 2.68 (t, J=6.4 Hz), (2.03 (m, 2H). 13 CNI-GABA 7.70 (d, J=8.9 Hz, 1H), 6.76 (d, J=8.9 Hz, 1H), 4.85 (s, 2H), 3.19 (t, J=8.2 Hz, 2H), 3.02 (t, J=7.1 Hz, 2H), 2.71 (t, J=6.8 Hz, 2H), 2.03-1.98 (m, 2H).

(1-[4-Aminobutanoyl]-5,7-dinitroindolin-4-yloxy)acetic acid 14 (CDNI-GABA). A solution of 11 (0.351 g, 1.53 mmol) in TFA was stirred with a nitronium ion source (e.g., sodium nitrate (15.5 mmol) in TFA) for 3d. The solvent was removed under a stream of nitrogen and then under high vacuum. The reaction mixture was dissolved in water and purified by HPLC (as above for CNI-Glu) to give CDNI-GABA (148 mg, 29% yield). NMR: δ (300 MHz, MeOD) 7.80 (s, 1H), 4.81 (s, 2H), 4.29 (t, J=7.1 Hz, 2H), 3.37 (t, J=7.1 Hz, 2H), 3.00 (t, J=6.8 Hz, 2H), 2.71 (t, J=6.3 Hz, 2H), 2.03-1.98 (m, 2H).

Quantum yield determination. The quantum yield for uncaging the new caged amino acids (CDNI-Glu, CNL-Glu, CNI-GABA and CNI-GABA) were measured by comparing the time of photolysis with the filtered (280-400 nm) output of a 500 W medium pressure Hg lamp of an equimolar solution (0.25 mM) of MNI-Glu and new cage. Inosine was used an inert internal standard. The path-length of the cuvette was 0.1 mm. The extent of reaction was monitored by HPLC as described previously (Huang, et al., 2005). A second method was employed to confirm these results: the time-course of change in UV-visible absorption spectra of each was compared to that of MNI-Glu (similar methods have been used for other caged glutamates: Fedoryak, et al., 2005 and Papageorgiou, et al., 2004). Both methods gave very similar results.

Electrophysiology. Hippocampal slices with a thickness of 300 μm were obtained from 15-18 day old Sprague-Dawley rats. A slice was transferred to recording chamber which was superfused with a solution containing (mM): 125 NaCl, 2.5 KCl, 1 $MgCl_2$, 2 $CaCl_2$, 1.25 $NaH_2PO_4$, 25 $NaHCO_3$, which was bubbled with 95% $O_2$ and 5% $CO_2$ gas. The bathing solutions also contained 1 μM tetrodotoxin, 50 μM picrotoxin and 200 μM Trolox (Aldrich). Whole-cell patch pipette contained a solution (mM): 135 Cs-gluconate, 5 $MgCl_2$, 1 $CaCl_2$, 2 ATP, 0.3 GTP, 0.5 fura-2, 10 TEA, 10 $Cs_4EGTA$, 10 Cs-HEPES at pH 7.2. All physiological experiments were performed at room temperature (23-25° C.).

2P imaging of dendritic spines was performed with an upright microscope (BX50WI; Olympus, Tokyo, Japan) equipped with a water immersion objective lens (LUMPlanFI/IR 60×, numerical aperture of 0.9) and with FLUOVIEW software (Olympus). Two mode-locked femtosecond-pulse Ti:sapphire lasers (Tsunami; Spectra Physics, Mountain View, Calif., USA) set at wavelengths of 720 and 830 nm were connected to the laser-scanning microscope via two independent scanheads. The laser at the wavelength of 830 nm was used for imaging of dendritic spines. Caged compounds were then applied locally from a glass pipette positioned close to the selected dendrite. Repetitive (1 or 2 Hz) photolysis of MNI-glutamate was performed at 720 nm with a pulse-train duration of 0.6 ms and a power of 4-20 mW at the specimen. A self-made program based on LabView (National Instruments, Austin, Tex., USA) controlled a galvano-scanner driver and a mechanical shutter (Uniblitz, Rochester, N.Y., USA). Neurons were voltage-clamped at −60 mV, and the currents were low-pass filtered at 2 kHz and sampled at 10 kHz. Series resistance was 33±7.4 MΩ (mean±s.d.) during mapping of AMPA receptors. For such mapping, a pseudorandom sequence of scanning of pixels in a region of interest was constructed to maintain the distance between two successive pixels greater than 2.5 to 5 μm and AMPA currents were sampled at an interval of 100 ms. These methods have been described before (Matsuzaki, et al., 2001, 2004).

| | NOVEL COMPOUNDS | |
|---|---|---|
| 5-CNI-glu | 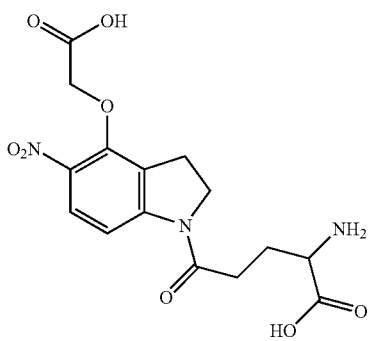 [SMILES: NC(CCC(=O)N1CCc2c1ccc([N+](=O)[O-])c2OCC(=O)O)C(=O)O] | Formula (V); compound 7 in FIG. 1 |
| CNI-glu | 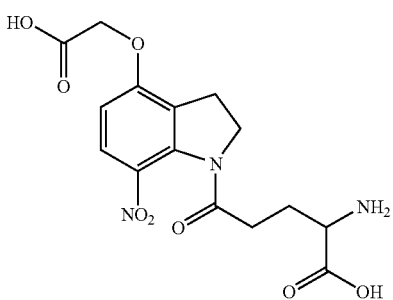 [SMILES: NC(CCC(=O)N1CCc2c(OCC(=O)O)ccc([N+](=O)[O-])c21)C(=O)O] | Formula (VI); compound 8 in FIG. 1 |
| CDNI-glutamate | 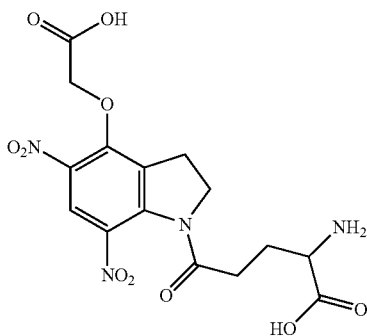 [SMILES: NC(CCC(=O)N1CCc2c(OCC(=O)O)c([N+](=O)[O-])cc([N+](=O)[O-])c21)C(=O)O] | Formula (III); compound 9 in FIG. 1 |
| 5-CNI-GABA | 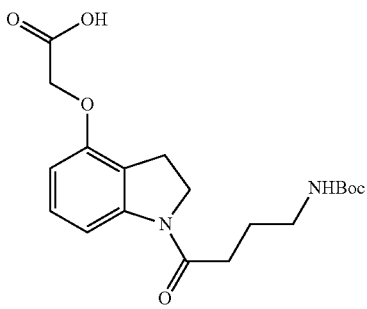 [SMILES: CC(C)(C)OC(=O)NCCCC(=O)N1CCc2c(OCC(=O)O)cccc21] | Formula (VII); compound 11 in FIG. 2 |
| CNI-GABA | 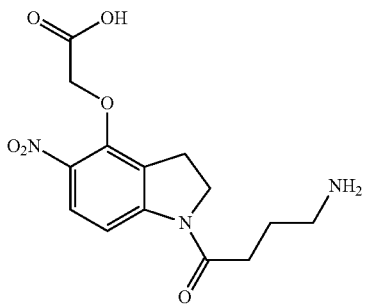 [SMILES: NCCCC(=O)N1CCc2c1ccc([N+](=O)[O-])c2OCC(=O)O] | Formula (VIII); compound 12 in FIG. 2 |

-continued

NOVEL COMPOUNDS

CNI-GABA — Formula (IX); compound 13 in FIG. 2

[Structure of CNI-GABA]

[Structure of second compound]

The invention will be illustrated in more detail with reference to the following Examples, but it should be understood that the present invention is not deemed to be limited thereto.

EXAMPLES

Example 1

Figure 5A:
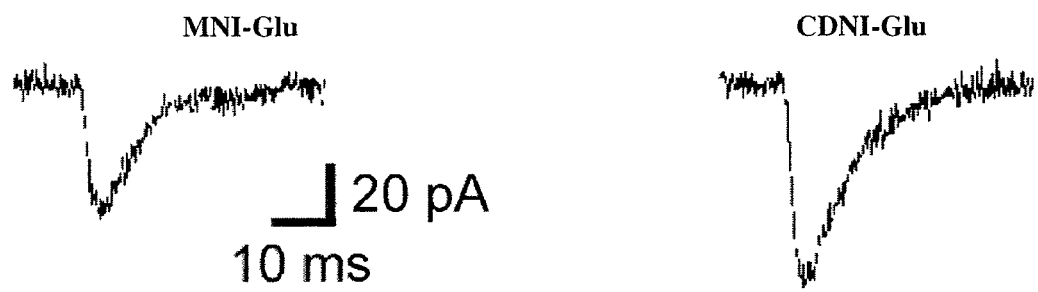
FIGS. 5A and 5B are current traces, demonstrating comparison of AMPA receptor currents evoked by 2-photon uncaging of MNI-Glu and CDNI-Glu on CA1 pyramidal neurons in acutely isolated brain slices. Top is image of neuron from slice of hippocampus Post-natal day 15 (P15) rat brain. MNI-Glu and CNDI-Glu were applied at 10 mM and 2.5 mM to the same neuron, and glutamate was uncaged in the image area at 3 power levels and 2 shutter times according to methods previously described in Matsuzaki, et al., 2001. The currents evoked by uncaging from CNDI-Glu were approximately 3-4 times larger than MNI-Glu, implying 12-16 times better reactivity for 2-photon uncaging.
Figure 5B:
Figure 5B:

AMPA receptor currents evoked by 2-photon uncaging of MNI-Glu and CDNI-Glu on CA1 pyramidal neurons in acutely isolated brain slices were compared. An image of neuron from slice of hippocampus Post-natal day 15 (P15) rat brain was obtained. MNI-Glu and CNDI-Glu were applied at 10 mM and 2.5 mM to the same neuron, and glutamate was uncaged in the image area at 2 power levels according to methods previously described in Matsuzaki, et al., 2001 (compare FIGS. 5A & 5B, MNI-Glu currents shown on right hand side, CDNI-Glu currents shown on left hand side). The currents evoked by uncaging from CNDI-Glu were approximately 2-3x larger than MNI-Glu, implying 5-10x better reactivity for 2-photon uncaging.

Example 2

Receptor currents evoked by 2-photon uncaging of CDNI-GABA, MNI-Glu and CNI-GABA on neurons in acutely isolated brain slices were compared. FIG. 4A demonstrated normal GABA-currents from spontaneous release of GABA at inhibitory synapses (so-called miniature inhibitory postsynaptic currents, or mIPSC) from hippocampal CA1 neurons from P18 rats. FIG. 4B demonstrated 2-photon evoked IPSC using 0.55 mM CDNI-GABA, 4 mW 720 nm light, for 1 ms irradiation (shutter) time; FIG. 4C demonstrated 2-photon uncaging of MNI-Glu (10 mM, 20 mW, 2 ms) on a different neuron; FIG. 4D demonstrated 2-photon uncaging of CNI-GABA on the same neuron as MNI-Glu under the same conditions.

It was observed that using only 4 mW of laser power, 2-photon uncaging of CDNI-GABA could evoke currents from neurons that were similar in size and duration that normal, physiological stimulation (compare currents traces in FIGS. 4A and 4B). Furthermore, on 2-photon uncaging of MNI-Glu or CNI-GABA on the same cell could be used to evoke excitatory or inhibitory currents, respectively (FIGS. 4C and 4D). Much larger powers and concentrations were required to obtain good signals using CNI-GABA as compared to CDNI-GABA. This reflects in part, the photolytic efficiency of the CDNI cage, and also the fact that at high concentrations CNI-GABA partially blocks uncaging GABA from binding to its receptor.

Example 3

Prophetic Examples of Synthesis

Dinitroindolinyl based caged photolabile compounds of the invention comprise a dinitroindolinyl caging moiety (I) (a chromophore) covalently linked to an effector moiety X as depicted by formula (II) below:

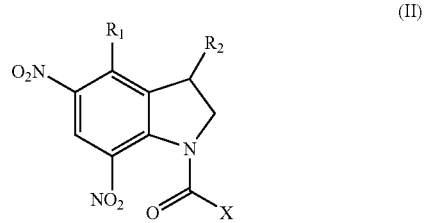

(II)

wherein X is a carboxylic acid and wherein $R_1$ is H, $O(CH_2)_n CO_2H$, $O(CH_2)_n OPO(OH)_2$, $O(CH_2)_n OSO_2(OH)$, $O(CH_2)_n$ C(O)NR$_3$, (CH$_2$)$_n$CO$_2$H, (CH$_2$)$_n$OPO(OH)$_2$, (CH$_2$)$_n$OSO$_2$(OH), (CH$_2$)$_n$C(O)NR$_3$, C$_{1-10}$ alkyl or substituted alkyl, O(CH$_2$)$_n$—Y, N(COZ)(CH$_2$)$_m$Y, or N[(CH$_2$)$_m$Q][(CH$_2$)$_n$Y], provided that R$_1$ is not OMe, R$_2$ is H, (CH$_2$)$_n$CO$_2$H, (CH$_2$)$_n$OPO(OH)$_2$, (CH$_2$)$_n$OSO$_2$(OH), (CH$_2$)$_n$C(O)NR$_3$ or (CH)$_n$N(R$_3$)$_2$, R$_3$ is H, Me, or Et, n and m are independently from 1 to 10, preferably n is from 1 to 5, Q and Y are independently selected from H, CO$_2$H or salts thereof, or OPO$_3^{2-}$, and Z is H, C$_{1-10}$ alkyl or substituted alkyl.

Exemplary dinitroindolinyl based caged photolabile compounds will now be described. The phosphate analog of CDNI-Glu could be synthesized as outlined in the scheme below.

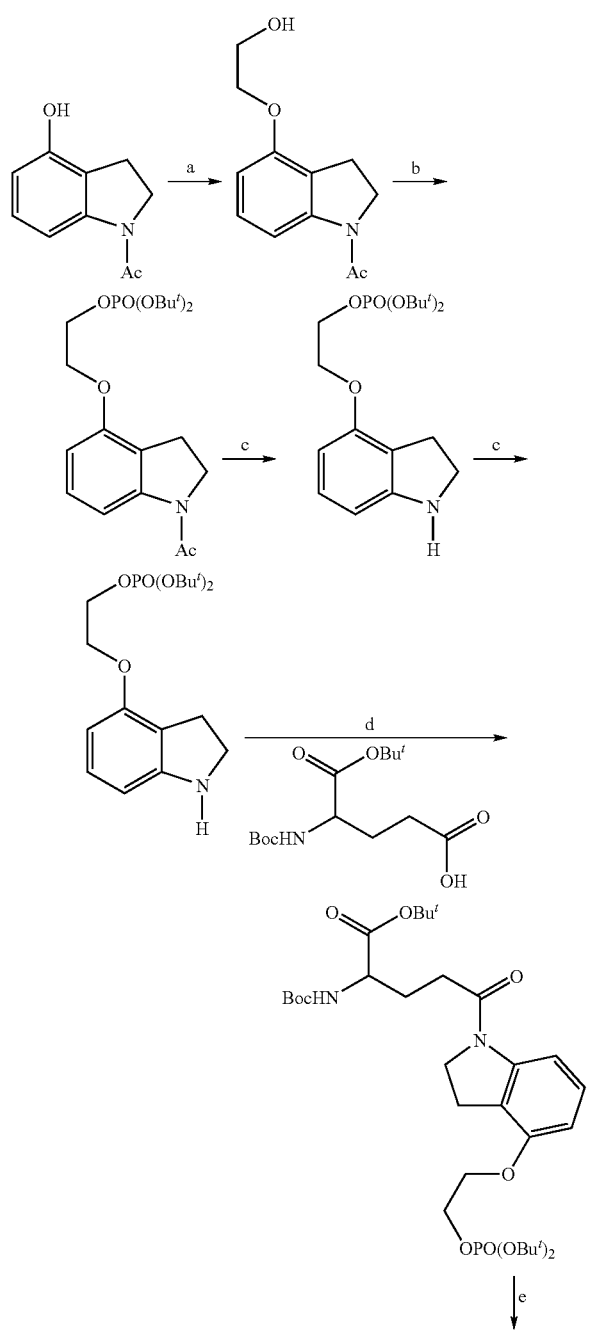

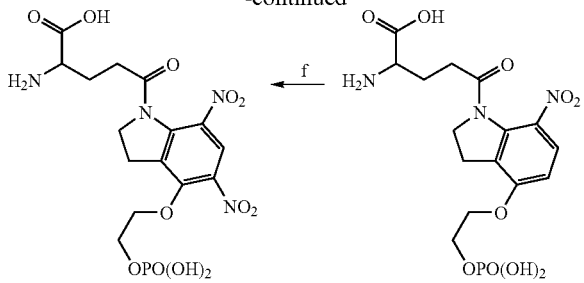

Starting with 1-acetyl-4-hydroxyindoline used for CDNI-Glu, step a would be a 2-carbon homologation at the 4-position with ethylene carbonate. A phosphate would then be added to resulting alcohol (step b) using di-tertiary-butylphosphoamidate with oxidation using hydrogenperoxide. The next step would be removal of the acetyl group with acid hydrolysis (step c), followed by carbodiimide coupling of the requisitely protected L-glutamate, just like CDNI-Glu synthesis (step d). (Caged GABA could be made by substituting the requisitely protected GABA, like CDNI-GABA.) The final 2 steps of the synthesis would be the same as CDNI-Glu: step e would be treatment with TFA, followed by 1.2 equivalents of NaNO$_3$. Purified material would then be nitrated with 20 equivalents of NaNO$_3$ to give phosphodinitroindolinyl-caged L-glutamate.

The amino analog of MDNI-Glu (Fedoryak, et al., 2005) could be made as outlined in the scheme below.

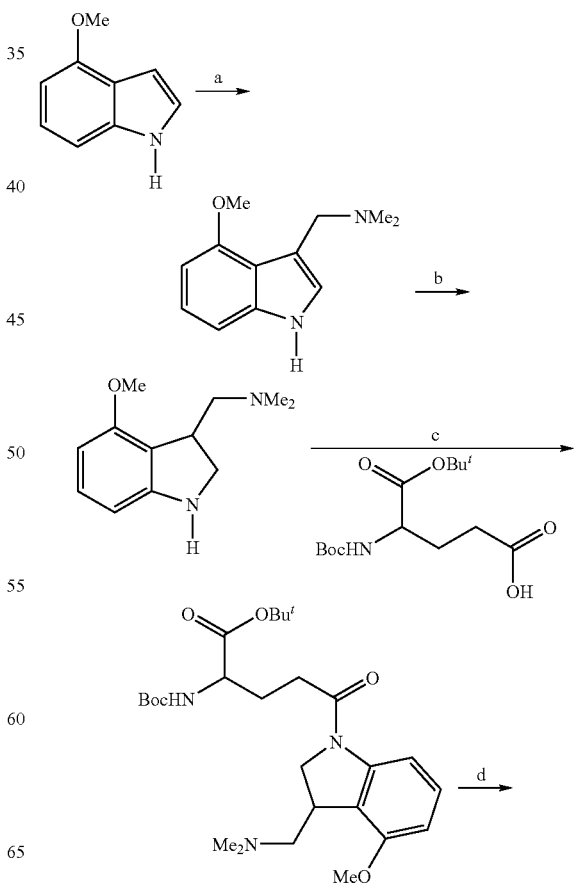

-continued

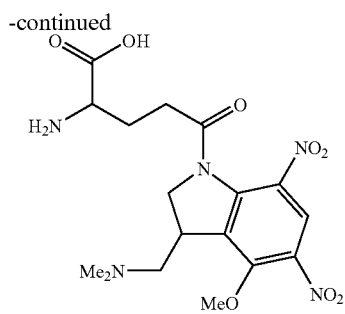

Starting with 4-methoxyindole, an amino substituents could be added at the 3-position using dimethylamine and formaldehyde in TFA (step a). The resulting indole would then be reduced to the indoline with borane (step b). The final steps are the same as those above: step c would be carbodiimide coupling of protected Glu, followed by sequential nitration (step d) using $NaNO_3$ in TFA, to give the amino-MDNI-Glu.

While the invention has been described in detail and with reference to specific examples thereof, it will be apparent to one skilled in the art that various changes and modifications can be made therein without departing from the spirit and scope thereof.

REFERENCES

1. Bernardinelli, Y., Haeberli, C., and Chatton, J. Y. Flash photolysis using a light emitting diode: an efficient, compact, and affordable solution. *Cell Calcium* 37, 565-572 (2005).
2. Burkat, P. M., Yang, J. and Gingrich, K. J. Dominant Gating Governing Transient GABAA Receptor Activity: A First Latency and Po/o Analysis. *J. Neurosci.* 21, 7026-7036 (2001).
3. Callaway, E. M. & Yuste, R. Stimulating neurons with light. *Curr. Op. Neurobiol.* 12, 587-592 (2002).
4. Canepari M, Nelson L, Papageorgiou G, Corrie J E, Ogden D: Photochemical and pharmacological evaluation of 7-nitroindolinyl- and 4-methoxy-7-nitroindolinyl-amino acids as novel, fast caged neurotransmitters. *J. Neurosci. Methods* 112:29-42 (2001).
5. Bloodgood, B. L. and Sabatini, B. L. Neuronal activity regulates diffusion across the neck of dendritic spines. *Science* (2005) 310: 866-869.
6. Carter A. G. & Sabatini, B. L. State-dependent calcium signaling in dendritic spines of striatal medium spiny neurons. *Neuron* 44, 483-493 (2004).
7. Denk, W. Two-photon scanning photochemical microscopy: mapping ligand-gated ion channel distributions. *Proc. Natl. Acad. Sci. USA* 91, 6629-6633 (1994).
8. Eder, M., Rammes, G., Zieglgansberger, W. and Dodt, H. U. GABA(A) and GABA(B) receptors on neocortical neurons are differentially distributed. *Eur. J. Neurosci.* 13, 1065-1069 (2001).
9. Ellis-Davies G C R Localized photolysis of caged compounds. *J. Gen. Physiol.* 114, 1a (1999).
10. Ellis-Davies G C R (2005) "Basics of photoactivation." in *Imaging in Neuroscience and Development: A Laboratory Manual* (2nd edition) eds. R. Yuste, and A. Konnerth (Cold Spring Harbor Laboratory Press, 2005).
11. Gee, K. R., Wieboldt, R. and Hess, G. P. Synthesis and photochemistry of a new Photolabile derivative of GABA. Neurotransmitter release and receptor activation in the millisecond time region. *J. Am. Chem. Soc.* 116, 8366-8367 (1994).
12. Fedoryak O, Sul J-Y, Haydon P G, and Ellis-Davies G C R Synthesis of a caged glutamate for efficient one and two-photon photorelease on living cells *Chem. Comm.* 3664-3666 (2005).
13. Furuta, T. et al. Brominated 7-Hydroxycoumarin-4-ylmethyls: Photolabile Protecting Groups with Biologically Useful Cross-sections for Two Photon Photolysis. *Proc. Natl. Acad. Sci. USA* 96, 1193-1200 (1999).
14. Gasparini S, Magee J C State-Dependent Dendritic Computation in Hippocampal CA1 Pyramidal Neurons. *J. Neurosci.* 26: 2068-2100 (2006).
15. Huang, Y. H. Sinha, S. R. Fedoryak, O. D. Ellis-Davies, G. C. R. & D. E. Bergles, D. E. "Synthesis and characterization of MNI-D-aspartate, a caged compound for selective activation of glutamate transporters and NMDA receptors in brain tissue." *Biochemistry* 44, 3316-3326 (2005).
16. Jayaraman, V., Shalita Thiran, S, and Hess, G. P. How Fast Does the γ-Aminobutyric Acid Receptor Channel Open? Kinetic Investigations in the Microsecond Time Region Using a Laser-Pulse Photolysis Technique. *Biochemistry* 38, 11372-11378 (1999).
17. Jones, M. V., Sahara, Y., Dzubay, J. A. and Westbrook, G. L. (1998) Defining affinity with the GABAA receptor. *J. Neurosci.* 18, 8590-8604.
18. Judkewitz, B., Roth, A. and Hausser, M. Dendritic enlightenment: using patterned two-photon uncaging to reveal the secrets of the brain's smallest dendrites. *Neuron* 50, 180-183 (2006).
19. Losonczyl A, and Magee, J. C. Integrative Properties of Radial Oblique Dendrites in Hippocampal CA1 Pyramidal Neurons. *Neuron* 50, 291-307 (2006).
20. Kasai H, Matsuzaki M, and Ellis-Davies G C R (2005) Two-photon uncaging microscopy. In: Yuste R, and Konnerth A (eds.) *Imaging in Neuroscience and Development: A Laboratory Manual* (2nd edition) pp. 375-384. Cold Spring Harbor, N.Y.: Cold Spring Harbor Laboratory Press.
21. Matsuzaki, M., Ellis-Davies, G. C. R., Nemoto, T., Miyashita, Y., Iino, M. & Kasai, H. Dendritic spine morphology is critical for AMPA receptor expression in hippocampal CA1 pyramidal neurons *Nat. Neurosci.* 4, 1086-1092 (2001).
22. Mozrzymas, J. W., Barberis, A., Mercik, K. and Zarnowska, E. D. Binding Sites, Singly Bound States, and Conformation Coupling Shape GABA-Evoked Currents. *J. Neurophysiol.* 89, 871-883 (2003).
23. Nusser, Z. Cull-Candy, S. and Farrant, M. Differences in synaptic GABAA receptor number underlie variation in GABA mini amplitude. *Neuron* 19, 697-709 (1997).
24. Papageorgiou, G. & Corrie, J. E. T. Effects of Aromatic substituents on the photocleavage of 1-acyl-7-nitroindolines. *Tetrahedron* 56, 8197-8205 (2000).
25. Papageorgiou G, Ogden D C, and Corrie J E T An antenna-sensitized nitroindoline precursor to enable photorelease of L-glutamate in high concentration. *Journal of Organic Chemistry* 69: 7228-7233 (2004).
26. Pettit, D. L. and G. J. Augustine (2000) Differential distribution of functional glutamate and GABA receptors in the dendrites of hippocampal pyramidal cells and interneurons. *J. Neurophysiol.* 84: 28-38.
27. Rabl, K., Cadetti, L. and Thoreson, W. B. Paired-pulse depression at photoreceptor synapses. *J Neurosci.* 2006 Mar. 1; 26(9):2555-63.
28. Shepherd, G. M. and Svoboda, K. Laminar and columnar organization of ascending excitatory projections to layer 2/3 pyramidal neurons in rat barrel cortex. *J Neurosci.* 25, 5670-9 (2005).
29. Sobczyk, A. Scheuss, V. & Svoboda, K. NMDA Receptor Subunit-Dependent $[Ca^{2+}]$ Signaling in Individual Hippocampal Dendritic Spines. *J. Neurosci.* 25, 6037-6046 (2005).

30. Wieboldt, R., Gee, K. Y., Niu, L., Ramash, D., Carpenter, B. K. & Hess, G. P. Photolabile precursors of glutamate: Synthesis, photochemical properties, activation of glutamate receptors in the microsecond time scale. *Proc. Natl. Acad. Sci. USA* 91, 8752-8756 (1994).
31. Schuddeboom, W. et al., Dipolar Triplet States of p-Nitroaniline and N-Alkyl Derivatives with One-, Two-, and Three-Fold Symmetry *J. Phys. Chem.* (1996) 100, 12369.
32. Katritzky et al., N-Acylbenzotriazoles: Neutral Acylating Reagents for the Preparation of Primary, Secondary, and Tertiary Amides Org. Chem. 2000; 65, 8210-8213.
33. Ellis-Davies, G. C. R. (2000) "Basics of photoactivation." in *Imaging Living Cells: A Laboratory Manual* eds. R. Yuste, F. Lanni and A. Konnerth (Cold Spring Harbor Laboratory Press, 2000)
34. Matsuzaki, M., N. Honkura, G. C. R. Ellis-Davies and H. Kasai "Structural basis of functional synaptic plasticity in single dendritic spines." *Nature* 2004, 429, 761.
35. Matsuzaki M, Ellis-Davies G C R, Nemoto T, et al. (2001) Dendritic spine geometry is critical for AMPA receptor expression in hippocampal CA1 pyramidal neurons. *Nature Neuroscience* 4: 1086-1093.
36. Denk, W., Piston, D. W. and Webb, W. W. (1995) "Two-photon molecular excitiation in laser-scanning microscopy." in Handbook of biological confocal microscopy ed. Pawley, J. B., Plenum Press, New York, pp. 445-458.
37. Shoham S, O'Connor D H, Sarkisov D V, Wang S S-H (2005) Rapid neurotransmitter uncaging in spatially defined patterns. Nat. Methods 2:837-43.
38. M. A. Smith, G. C. R. Ellis-Davies and J. C. Magee "Synaptic mechanisms of the distance-dependent scaling of schaffer collateral synapses in CA1 pyramidal neurons." *J. Physiol.* 2003, 548, 245
39. J. Noguchi, M. Matsuzaki, G. C. R. Ellis-Davies and H. Kasai "Spine-neck geometry determines NMDA-receptor dependent Ca signaling in dendrites." *Neuron* 2005, 46, 609.

What is claimed is:

1. A photolabile compound depicted by the formula:

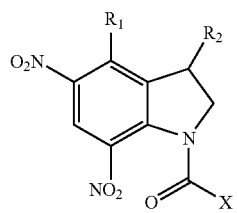

(II)

wherein:

$R_1$ is $O(CH_2)_nCO_2H$, $O(CH_2)_nOPO(OH)_2$, $O(CH_2)_nOSO_2(OH)$, $O(CH_2)_nC(O)NR_3$, $(CH_2)_nCO_2H$, $(CH_2)_nOPO(OH)_2$, $(CH_2)_nOSO_2(OH)$, $(CH_2)_nC(O)NR_3$, $C_{1-10}$ alkyl or substituted alkyl, $O(CH_2)_nM$, $N(COZ)(CH_2)_mY$, or $N[(CH_2)_mQ][(CH_2)_nY]$, $R_2$ is H, $(CH_2)_nCO_2H$, $(CH_2)_nOPO(OH)_2$, $(CH_2)_nOSO_2(OH)$, $(CH_2)_nC(O)NR_3$ or $(CH)_nN(R_3)_2$, $R_3$ is H, Me or Et, n and m are independently from 1 to 10, Q and Y are independently selected from H, $CO_2H$ or salts thereof, or $OPO_3^{2-}$, M is selected from $CO_2H$ or salts thereof, or $OPO_3^{2-}$, Z is H, $C_{1-10}$ alkyl or substituted alkyl, and X is a non-carboxyl portion of a carboxylic acid.

2. The photolabile compound of claim 1, wherein the carboxylic acid is a neuroactive amino acid.

3. The photolabile compound of claim 2, wherein the neuroactive amino acid is at least one of L-glutamate, gamma-aminobutyric acid, D-aspartate and glycine.

4. A photolabile compound represented by one of the following formulas:

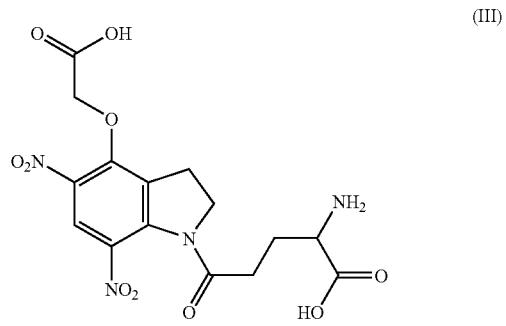

(III)

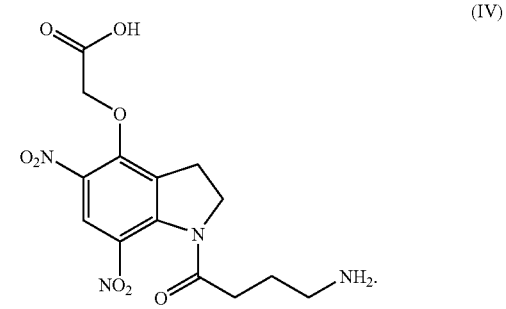

(IV)

5. A photolabile compound selected from the group consisting of:

(a) 5-CNI-glu

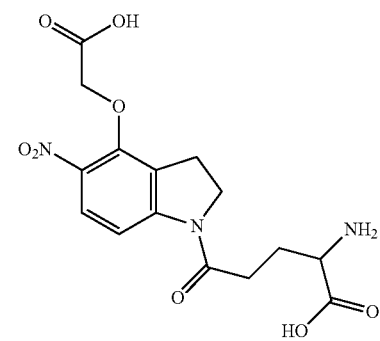 [SMILES: NC(CCC(=O)N1CCc2c1ccc([N+](=O)[O-])c2OCC(=O)O)C(=O)O]

Formula (V);

| | | | |
|---|---|---|---|
| (b) | CNI-glu | 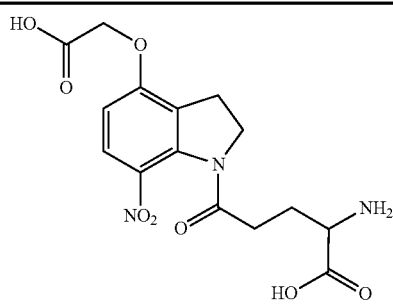 | Formula (VI); |
| (c) | 5-CNI-GABA | 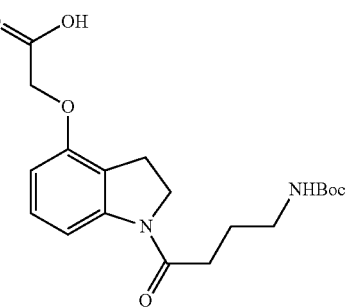 | Formula (VII); |
| (d) | CNI-GABA | 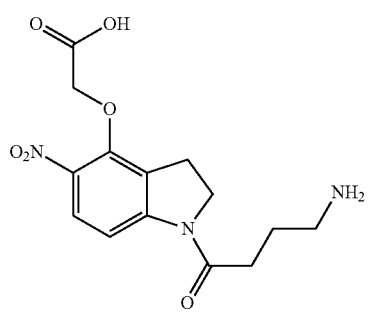 [SMILES: NCCCC(=O)N1CCc2c1ccc([N+](=O)[O-])c2OCC(=O)O] | Formula (VIII); and |
| (e) | CNI-GABA | 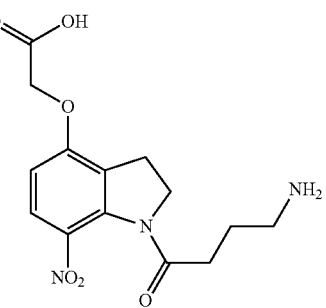 | Formula (IX). |
* * * * *

UNITED STATES PATENT AND TRADEMARK OFFICE
CERTIFICATE OF CORRECTION

PATENT NO. : 8,642,785 B2
APPLICATION NO. : 12/520924
DATED : February 4, 2014
INVENTOR(S) : Ellis-Davies It is certified that error appears in the above-identified patent and that said Letters Patent is hereby corrected as shown below:

In the Specification

Column 1, in the section entitled "STATEMENT REGARDING FEDERALLY SPONSORED RESEARCH OR DEVELOPMENT" please amend the statement below the title to add additional National Institute of Health Grant number GM053395. The new statement should read as shown below:

This research was supported in part by U.S. Government funds (National Institute of Health, Grant No. 1 R24 GM65473-02 and Grant No. GM053395) and the U.S. Government may therefore have certain rights in the invention.

Signed and Sealed this
Second Day of September, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,642,785 B2  Page 1 of 1
APPLICATION NO. : 12/520924
DATED : February 4, 2014
INVENTOR(S) : Graham Ellis-Davies It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 471 days.

Signed and Sealed this

Twenty-ninth Day of September, 2015

Michelle K. Lee
*Director of the United States Patent and Trademark Office*